US009855021B2

(12) United States Patent
Abraham

(10) Patent No.: US 9,855,021 B2
(45) Date of Patent: *Jan. 2, 2018

(54) IMAGE GUIDED CATHETERS AND METHODS OF USE

(71) Applicant: Perceptive Navigation, LLC, Baltimore, MD (US)

(72) Inventor: Theodore P. Abraham, Baltimore, MD (US)

(73) Assignee: Perceptive Navigation, LLC, Baltimore, MD (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/865,151

(22) Filed: Sep. 25, 2015

(65) Prior Publication Data

US 2016/0081656 A1     Mar. 24, 2016

Related U.S. Application Data

(63) Continuation-in-part of application No. 13/847,902, filed on Mar. 20, 2013, now Pat. No. 9,149,257, and
(Continued)

(51) Int. Cl.
*A61B 8/00*     (2006.01)
*A61B 8/12*     (2006.01)
(Continued)

(52) U.S. Cl.
CPC .............. *A61B 8/12* (2013.01); *A61B 8/0841* (2013.01); *A61B 8/445* (2013.01); *A61B 8/4483* (2013.01);
(Continued)

(58) Field of Classification Search
None
See application file for complete search history.

(56) References Cited

U.S. PATENT DOCUMENTS 3,556,079 A    1/1971   Omizo
3,612,050 A   10/1971   Sheridan
(Continued)

FOREIGN PATENT DOCUMENTS

CA     2376103     3/2001
DE     19939791     2/2001

*Primary Examiner* — Joel F Brutus
(74) *Attorney, Agent, or Firm* — Cameron LLP

(57) ABSTRACT

An interventional medical device is provided that incorporates a forward-directed ultrasound imaging system integrated into a single minimally invasive device. The medical device can be in the form of an image guided catheter having a replaceable and reusable ultrasound imaging assemble and replaceable interventional devices such as a removable introducer needle and syringe, the device having a tapered distal tip, particularly those suitable for minimally invasive direct introduction into the human or other mammalian body. The imaging system comprises one or more small ultrasound transducers that can be replaceably integrated into the device via a longitudinal slot in an expendable elongate body and may be inserted into and removed from the device to customize the device for a particular use. An ultrasound system can be provided in the device either alone or in combination with fiber optic imaging to provide a range of forward imaging and therapeutic capabilities of the device for direct access to a target site from the skin via the removable introducer needle.

21 Claims, 11 Drawing Sheets

Related U.S. Application Data a continuation-in-part of application No. 13/973,476, filed on Aug. 22, 2013, said application No. 13/847,902 is a continuation of application No. 11/871,282, filed on Oct. 12, 2007, now Pat. No. 8,403,859, and a continuation-in-part of application No. 11/782,991, filed on Jul. 25, 2007, now Pat. No. 8,403,858.

(60) Provisional application No. 60/851,451, filed on Oct. 12, 2006, provisional application No. 61/692,443, filed on Aug. 23, 2012.

(51) Int. Cl.
  *A61B 10/04* (2006.01)
  *A61M 25/00* (2006.01)
  *A61B 8/08* (2006.01)
  *A61B 17/34* (2006.01)

(52) U.S. Cl.
  CPC .............. *A61B 8/565* (2013.01); *A61B 8/582* (2013.01); *A61B 10/04* (2013.01); *A61M 25/0026* (2013.01); *A61B 8/0808* (2013.01); *A61B 2017/3413* (2013.01)

(56) References Cited

U.S. PATENT DOCUMENTS

| | | | |
|---|---|---|---|
| 4,092,867 A | 6/1978 | Matzuk | |
| 4,327,709 A | 5/1982 | Hanson et al. | |
| 4,540,411 A * | 9/1985 | Bodicky | A61M 39/0613 251/4 |
| 4,869,258 A | 9/1989 | Hetz | |
| 5,011,469 A | 4/1991 | Buckberg et al. | |
| 5,106,368 A | 4/1992 | Uldall et al. | |
| 5,159,931 A | 11/1992 | Pini | |
| 5,181,514 A | 1/1993 | Solomon et al. | |
| 5,454,373 A | 10/1995 | Koger et al. | |
| 5,505,088 A | 4/1996 | Chandraratna et al. | |
| 5,509,909 A | 4/1996 | Moy | |
| 5,701,901 A | 12/1997 | Lum et al. | |
| 5,704,361 A | 1/1998 | Seward et al. | |
| 5,967,984 A | 10/1999 | Chu et al. | |
| 5,997,497 A | 12/1999 | Nita et al. | |
| 6,068,638 A | 5/2000 | Makower | |
| 6,149,598 A | 11/2000 | Tanaka | |
| 6,162,179 A | 12/2000 | Moore | |
| 6,254,573 B1 | 7/2001 | Haim et al. | |
| 6,306,097 B1 | 10/2001 | Park et al. | |
| 6,572,551 B1 | 6/2003 | Smith et al. | |
| 6,582,390 B1 | 6/2003 | Sanderson | |
| 6,592,559 B1 | 7/2003 | Pakter et al. | |
| 6,685,648 B2 | 2/2004 | Flaherty | |
| 6,689,062 B1 | 2/2004 | Mesallum | |
| 6,726,677 B1 | 4/2004 | Flaherty et al. | |
| 7,100,614 B2 | 9/2006 | Stevens et al. | |
| 7,270,634 B2 | 9/2007 | Scampini et al. | |
| 7,488,289 B2 | 2/2009 | Suorsa et al. | |
| 7,713,190 B2 | 5/2010 | Brock et al. | |
| 7,860,555 B2 | 12/2010 | Saadat | |
| 2001/0023323 A1 | 9/2001 | Nishtala et al. | |
| 2002/0077568 A1* | 6/2002 | Haddock | A61B 5/1076 600/587 |
| 2002/0123698 A1 | 9/2002 | Garibotto et al. | |
| 2003/0139677 A1 | 7/2003 | Fonseca et al. | |
| 2003/0199767 A1* | 10/2003 | Cespedes | A61B 5/01 600/473 |
| 2003/0229286 A1* | 12/2003 | Lenker | A61B 8/12 600/462 |
| 2004/0015193 A1 | 1/2004 | Lamson et al. | |
| 2004/0102804 A1* | 5/2004 | Chin | A61B 17/00008 606/190 |
| 2005/0090709 A1 | 4/2005 | Okada et al. | |
| 2005/0096642 A1* | 5/2005 | Appling | A61B 18/24 606/15 |
| 2005/0143664 A1 | 6/2005 | Chen et al. | |
| 2006/0106315 A1 | 5/2006 | Edens | |
| 2007/0293724 A1 | 12/2007 | Saadat et al. | |

\* cited by examiner

IMAGE GUIDED CATHETERS AND METHODS OF USE

CROSS-REFERENCE

This application is a continuation-in-part of U.S. patent application Ser. No. 13/847,902 filed Mar. 20, 2013 (now allowed), which is a continuation of U.S. patent application Ser. No. 11/871,282 filed Oct. 12, 2007 (now U.S. Pat. No. 8,403,859 issued Mar. 26, 2013) and a continuation-in-part of U.S. patent application Ser. No. 11/782,991 filed Jul. 25, 2007 (now U.S. Pat. No. 8,403,858 issued Mar. 26, 2013), both of which patent applications claim priority to provisional U.S. Application Ser. No. 60/851,451 filed Oct. 12, 2006, and is a continuation-in-part of U.S. patent application Ser. No. 13/973,476 filed Aug. 22, 2013, which claims the benefit of priority to U.S. provisional patent application Ser. No. 61/692,443, filed Aug. 23, 2012, entitled Remote Assessment System, all applications of Theodore P. Abraham, the disclosures of all priority applications being hereby incorporated by reference into the present application in their entirety.

TECHNICAL FIELD

Embodiments of the illustrated and disclosed aspects and features relate to minimally invasive interventional medical devices having removable and/or reusable components of an ultrasound imaging system, and, more particularly, to an ultrasound image guided catheter and methods of use, the catheter having a removable and reusable ultrasound transducer assembly component and a removable and replaceable needle assembly component, the transducer assembly being replaceable with transducer assemblies with ultrasound transducers having higher or lower frequency ranges and the needle assembly being replaceable with instruments for use at a target site for a medical procedure.

BACKGROUND

Ultrasound operates by creating an image from sound in three steps—producing a sound wave, receiving echoes, and interpreting those echoes to create an image.

Ultrasound has many uses in medical applications. For example, ultrasound is routinely used during pregnancy to provide images of the fetus in the womb. Generally, a water-based gel is applied to the patient's skin, and a hand-held probe, called a transducer, is placed directly on and moved over the patient. The probe typically contains a piezoelectric element that vibrates and generates a sound wave when a current is applied. In ultrasound devices, the sound wave is typically produced by creating short, strong vibrational pulses using the piezoelectric transducer. The sound wave is reflected from tissues and structures and returns an echo, which vibrates the transducer elements and turns the vibration into electrical pulses. The electrical pulses are then sent to an ultrasound scanner having a display where they are transformed into a viewable analog or digital image on the display.

While general-purpose ultrasound machines may be used for most imaging purposes, certain procedures require specialized apparatus. For example, in a pelvic ultrasound, organs of the pelvic region can be imaged using either external or internal ultrasound. In contrast, echocardiography, which is used in cardiac procedures, can require specialized machines to take into account the dynamic nature of the heart.

Ultrasound has advantages over other imaging methods such as magnetic resonance imaging (MRI) and computed tomography (CT). For example, ultrasound is relatively inexpensive compared to those techniques. Ultrasound also is capable of imaging muscle and soft tissue very well, can delineate interfaces between solid and fluid filled spaces, and may show the structure of organs. Ultrasound renders live images and can be used to view the operation of organs in real time. Ultrasound has no known long-term side effects and generally causes little to no discomfort to a patient. Further, ultrasound equipment is widely available, flexible and portable.

However, ultrasound does have some drawbacks. When used on obese patients, image quality is compromised as the overlying adipose tissue scatters the sound and the sound waves are required to travel greater depths, resulting in signal weakening on transmission and reflection back to the transducer. Even in non-obese patients, depth penetration is limited, thereby making it difficult to image structures located deep within the body. Further, ultrasound has trouble penetrating bone and, thus, for example, ultrasound imaging of the brain within skull bone is limited from external to an animal body. Ultrasound also does not perform well when there is gas present (as in the gastrointestinal tract and lungs). Still further, a highly skilled and experienced ultrasound operator is necessary to obtain quality images. These drawbacks do not, however, limit the usefulness of ultrasound as a medical diagnostic and treatment tool.

The use of ultrasonic apparatus for imaging areas of the human body, either alone or in combination with other instruments, is known, for example, for guiding therapeutic instruments through a catheter to a field of view within a human body. For example, ultrasound devices have been combined with catheters for insertion into a body, usually through a vein or artery, to reach a part of the human body for examination or treatment. Such devices are commonly known in the art as "imaging catheters."

For example, U.S. Pat. No. 5,704,361 to Seward et al. discloses a volumetric image ultrasound transducer underfluid catheter system. For example, FIGS. 2-9 and 11-12 of Seward et al. and their attendant description suggest specific methods of intervention for imaging purposes in the vicinity of a human heart. To reach such an area of interest within a human body, an ultrasound imaging and hemodynamic catheter may be advanced via the superior vena cava to a tricuspid valve annulus. A distal end of a cylindrical body includes a guide wire access port and a guide wire provides a means of assuring that the catheter reaches a target for imaging. A surgical tool may be fed through the catheter to the area imaged.

U.S. Pat. No. 6,572,551 to Smith et al. provides another example of an imaging catheter. Tools such as a suction device, guide wire, or an ablation electrode, may be incorporated in an exemplary catheter according to Smith et al.

U.S. Pat. No. 5,967,984 to Chu et al. describes an ultrasound imaging catheter with a cutting element which may be an electrode wire or a laser fiber. FIGS. 1 and 2 of Chu et al. also describe a balloon 14 and a means to inflate the balloon. The balloon, for example, may be utilized to dilate a vessel having strictures imaged via the imaging catheter.

Other imaging catheters are known. For example, U.S. Pat. No. 6,162,179 to Moore teaches bending (using a pull wire) an acoustic window into a known and repeatable arc for improved three dimensional imaging. U.S. Pat. No. 6,306,097 to Park et al. discloses an intravascular ultrasound imaging catheter whereby a first lumen provides access for an ultrasound imaging catheter and a second lumen provides a working port for a tool. U.S. Pat. No. 5,505,088 to Chandraratna et al. teaches using a 200 MHz transducer in an ultrasonic microscope combined with a catheter as a delivery means for the microscope to provide imaging of myocardial tissue. According to Chandraratna et al., lower frequency ultrasound transducers can provide deeper penetration in the tissue but do not provide the image quality provided by higher frequencies.

All the above-cited references are incorporated by reference as to any description which may be deemed essential to an understanding of illustrated and discussed aspects and embodiments of devices and methods herein and as summarized below.

SUMMARY OF THE EMBODIMENTS

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter.

A device in accordance with one or more aspects described herein can include ultrasound imaging using a conventional piezoelectric linear or phased array transducer or more recently developed all-optical ultrasound transducer high resolution imaging or optical imaging through the use of fiber optics through an additional channel or lumen, or a combination of these, to provide a wide range of imaging capabilities coupled with one or more diagnostic, therapeutic, or interventional capabilities. In one or more embodiments according to aspects herein, an interventional ultrasound device may include an expendable housing (useful for one minimally invasive medical procedure) having a proximal end and a distal end, first lumen, also referred to as an imaging lumen, for an imaging ultrasound transducer, a second lumen which extends to a distal tip of the expendable housing, also referred to as a needle lumen, for receiving a removable needle or other interventional device, and an imaging transducer assembly adapted to removably fit into the imaging lumen at the distal end of the housing that can be removed, reused, and/or replaced with imaging transducer assemblies having ultrasound transducers of higher or lower frequency ranges and adapted to be used for different purposes in real time, for example, during a medical procedure.

Illustrative aspects described herein include a minimally invasive interventional medical device that can provide ultrasound imaging coupled together with one or more interventional capabilities. The ultrasound frequencies present in a sound wave output by such a device can range between 20 KHz and several hundred MHz. Frequencies in the lower range, for example, below 1 MHz, and particularly in the 100-200 KHz range, can be used, for example, to provide heat therapy or to treat conditions such as blood clots and provide low resolution, long range imaging. Frequencies above 1 MHz can be used to provide higher resolution imaging at shorter range. For example, frequencies in the 25-30 MHz range can be used to image organs such as the eye or can be used to provide imaging of small animals. Higher frequencies, for example, ultrasound frequencies in the 100 to several hundred MHz range, can be used to provide even higher-resolution imaging, sometimes known as high-frequency ultrasound microscopy, at a target site within a body undergoing a medical procedure.

An embodiment of a device in accordance with one or more aspects and features described herein can include a reusable, removable ultrasonic imaging device assembly having one or more forward-directed ultrasound transducers that can be inserted into a distal end of an expendable catheter housing by way of a lengthwise slot in the proximal end of the housing so as to provide access to the distal end of the housing from which, when the ultrasonic imaging device assembly is moved forward into the distal end and operated, a direct forward view of the tissue being accessed may be obtained from the ultrasonic imaging device assembly and displayed on a display. An embodiment of a device in accordance with one or more aspects and features described herein may comprise a minimally invasive image guided catheter device having a removable, replaceable introducer needle assembly in the needle lumen and then the one or more replaceable forward-directed ultrasound transducer assemblies that can be inserted and moved forward into the imaging lumen of a single expendable housing via the lengthwise slot at the proximate end so that the introducer needle and the imaging catheter (expendable) housing along with the replaceable transducer assembly can be introduced into a body substantially simultaneously. The introducer needle (or instruments replacing the needle), the distal tip of the housing and the path taken by the needle can be viewed within an imaging zone of the replaceable transducer assembly as the entire assembly comprising transducer assembly, housing and syringe/needle assembly components travels through an animal body to a target site for a medical procedure. An alternative embodiment of a device (shown in priority patent applications) in accordance with aspects described herein can have one or more ultrasonic transducers located along one or more sides of the image guided transducer assembly and housing to obtain peripheral views of the body under medical procedure. The replaceable imaging transducer assembly and removable introducer needle assembly may comprise a forward-directed ultrasound transducer imaging assembly operating within, for example, a first and second predetermined range of frequencies to enter the human body, then guide the entire image guided catheter to the target site of a medical procedure and provide high resolution imaging at the target site.

The ultrasound features of the device can serve to guide and facilitate surgical procedures performed with the image guided catheter device. For example, a medical professional such as a surgeon can receive direct high resolution vision of a targeted area in real time. The lumen for receiving the syringe and introducer needle assembly may have inserted and locked into place therein a hollow syringe needle for withdrawing unwanted fluids or tissue specimens or use a tapered solid needle for, for example, skin penetration and internal body wall puncture.

A wide variety of other interventional elements also can be incorporated into such a device. Examples of replacements for a syringe/needle assembly in the needle lumen may include a syringe having a biopsy needle, an instrument including a biopsy blade, an instrument carrying a micromotive electronic manipulator (MEMS) device, an instrument comprising a clasper for clasping tissue and other instruments as described in priority patent applications and issued patents. A syringe needle may be hollow or solid and may be used as an introducer needle and for delivering medication or for removing unwanted fluid (for example unwanted fluid in the pericardial sac).

For example, in some embodiments of a device in accordance with one or more aspects and features described herein, an ultrasound imaging transducer assembly can be combined with an interventional catheter having an introducer needle so that the catheter distal end can be inserted under ultrasound imaging guidance directly into the target site (the proximal end being used by medical personnel to grasp the assembled image guided catheter device). For example, the image guided catheter can be inserted directly through the chest wall and into the heart using the introducer needle without having to make entry through another means such as through a blood vessel in a human leg or by using a guide wire as is taught with prior art devices. If necessary, an ultrasound transducer assembly having a longer range and lower resolution may be replaced in real time during the movement of the image guided catheter assembly with a higher resolution and shorter range transducer assembly as the target site is reached. Once at the target location for a medical procedure, the removable needle may be removed and replaced with another instrument such as a biopsy needle, MEMS device, tissue clasper or biopsy blade among other instruments.

In another embodiment in accordance with one or more aspects herein, a medical device is provided that can comprise one or more ultrasound transducers coupled or associated with a syringe element for delivery of medication or withdrawal of unwanted fluids at a treatment site. An exemplary syringe that may be used to replace an introducer needle assembly once the device is at the target site is a needle assembly such as is described in U.S. Pat. No. 6,592,559 to Pakter et al., which may deliver multiple needles to multiple sites within the body at the target site.

According to other aspects, at the proximal end of such a device, an anchoring portion may be provided for anchoring the device to a human body once the device is image-guided to the diagnosis or treatment site. The proximal end may also include locking mechanisms for securing the removable, replaceable imaging transducer assembly and/or a syringe with another medical device or instrument of the expendable housing component while the image catheter device is in use during a medical procedure.

According to aspects herein, the housing of such a device may be formed from one or more of a variety of materials such as silicone, Teflon, polyurethane, PVC, TPX, and/or elastomeric hydrogel. According to some aspects, the housing may be cylindrical in shape and may include, for example, a catheter or vascular sheath. The expendable housing may be tapered at the distal end. According to some aspects, the housing may have a lengthwise slot opening on one side allowing its user to freely insert and remove the replaceable imaging transducer assembly while the image guided catheter device is being used for a minimally invasive medical procedure.

According to aspects herein, the imaging transducer assembly may comprise a forward viewing phased array probe with a variable field of view depending on the specific array. The imaging transducer assembly may comprise an ultrasound transducer at the distal end with variable frequency, variable cross-sectional diameter, and a variable number of transducer elements located in a steel or rigid plastic cylinder with a varying outer diameter, for example, wherein the expendable housing may have two or three different outer diameters (shown) during its length from a large outer diameter at the proximal end of the expendable housing to a very small outer diameter at the distal end.

According to aspects herein, the syringe/needle assembly lumen may fit a removable variable gauge solid introducer needle, a hollow syringe needle (shown) or other interventional instruments as discussed above once the operating target site is reached.

These and other aspects of embodiments of an image guided catheter assembly will be discussed with reference to the drawings, a brief description of which follows.

BRIEF DESCRIPTION OF THE DRAWINGS

FIG. 2A shows the patient end of the imaging catheter with a removable introducer needle protruding from the needle lumen which needle may be hollow (shown) or solid and may be tapered as shown to match the degree of taper of the tapered distal end. The introducer may comprise a portion of a syringe for a biopsy needle for collecting body tissue or for withdrawing unwanted fluid. The imaging lumen 214 and tapered face 213 are seen at the top in which has been located and locked into place the ultrasound transducer assembly as will be discussed with reference to FIGS. 3A, 3B and 3C. FIG. 2B shows the same view with the outer plastic of the imaging lumen and the outer shell of the imaging transducer assembly shown as transparent to show the ultrasound transducer assembly component and leads/wires/channels inside the removable and replaceable imaging transducer assembly. Note that in each of FIGS. 2A and 2B an imaging face 213 of an imaging lumen is provided which may match the impedance of body tissue and be sufficiently thin and comprise a material to provide a large imaging zone as seen in FIG. 1. An alternative embodiment with an open distal end face 213 and imaging lumen is shown, for example, in FIG. 10 having a thin imaging window component 711 just in front of the transducer 210 for matching impedance and improving the imaging zone as displayed on a display.

FIG. 3A is a left side view of the expendable catheter housing 301 with the imaging transducer assembly 304 in position beside the catheter housing ready to be inserted into a longitudinal slit opening 306 at the proximal, surgeon end of the housing. FIG. 3B is the same view showing the imaging transducer assembly component 304 inserted into the lengthwise slot 306 horizontally toward the center of the housing to align the transducer element or elements for subsequent movement towards the distal tip 309 of the expendable housing 301 and within the imaging lumen of the enclosed distal end 309 of minimum diameter. FIG. 3C shows the imaging transducer assembly moved forward lengthwise towards the distal tip of the expendable housing and, then, locked into position for use via clasp 321 and receiver 322. For the entire length of the distal end 309, the transducer assembly component 304 is enclosed within the imaging lumen 314 comprising, for example, circular side walls and either a window per FIG. 10 or an enclosed tapered tip face of the imaging lumen (FIG. 2A), the window or enclosed tapered tip for preventing body fluid or tissue from touching the reusable transducer assembly component 304 and permitting replacement with another transducer assembly component during a medical procedure, if needed.

FIG. 4A shows the imaging transducer assembly about to be secured to the proximal end of the housing via the locking mechanism 321,322, and FIG. 4B shows the imaging transducer assembly secured to the housing at the proximal end by such a locking mechanism.

FIG. 5A shows the syringe with a removable introducer needle being inserted into the proximal end of the housing, and FIG. 5B shows the edge of the syringe secured to the expendable housing at the proximal end lip 324 being caught in a slot of tab 326.

FIG. 6A, for example, shows the syringe and the device in an unlocked position before lip 323 is caught by tab 326, and FIG. 6B shows the syringe and the imaging device in a locked position. The syringe with a solid or hollow needle may be replaced by another medical instrument once the image guided catheter assembly distal end has reached the target site of the medical procedure.

FIG. 8A(1) depicts a perspective right side view and FIG. 8A(2) depicts a perspective left side view. FIG. 8B(1) depicts a top view, FIG. 8B(2) depicts a lengthwise cross-section from the distal tip to the larger outer diameter proximal end adapted to be held by a surgeon, FIG. 8B(3) depicts a right side view, FIG. 8B(4) depicts a widthwise cross-section E-E of FIG. 8B(3) near the distal tip showing the imaging lumen and the needle lumen, FIG. 8B(5) depicts a front view where the distal tip of the housing is referred to as the front, FIG. 8B(6) depicts a front view along section D-D where the distal end is referred to as the front of the image guided catheter housing, and FIG. 8B(7) depicts a rear view where the proximal end of the housing is referred to as the rear of the image guided catheter housing.

FIG. 9A(1) depicts a perspective right side view, FIG. 9A(2) depicts a perspective left side view, and FIG. 9A(3) depicts a top view. FIG. 9B(1) depicts a right side view, FIG. 9B(2) depicts a widthwise cross-section near the distal tip showing the imaging lumen and needle lumen, FIG. 9B(3) depicts a front view where the distal tip is the front, FIG. 9B(4) depicts a rear view where the proximal tip is the rear, and FIG. 9B(5) depicts a widthwise cross-section near the proximal tip.

FIG. 10(1) depicts a perspective right side view. FIG. 10(2) depicts a cross-section from the right side. FIG. 10(3) depicts a perspective left side view. FIG. 10(4) depicts a front view. FIG. 10(5) depicts a right side view. FIG. 10(6) depicts a rear view. FIG. 10(7) depicts a top view.

DETAILED DESCRIPTION

Figure 1:
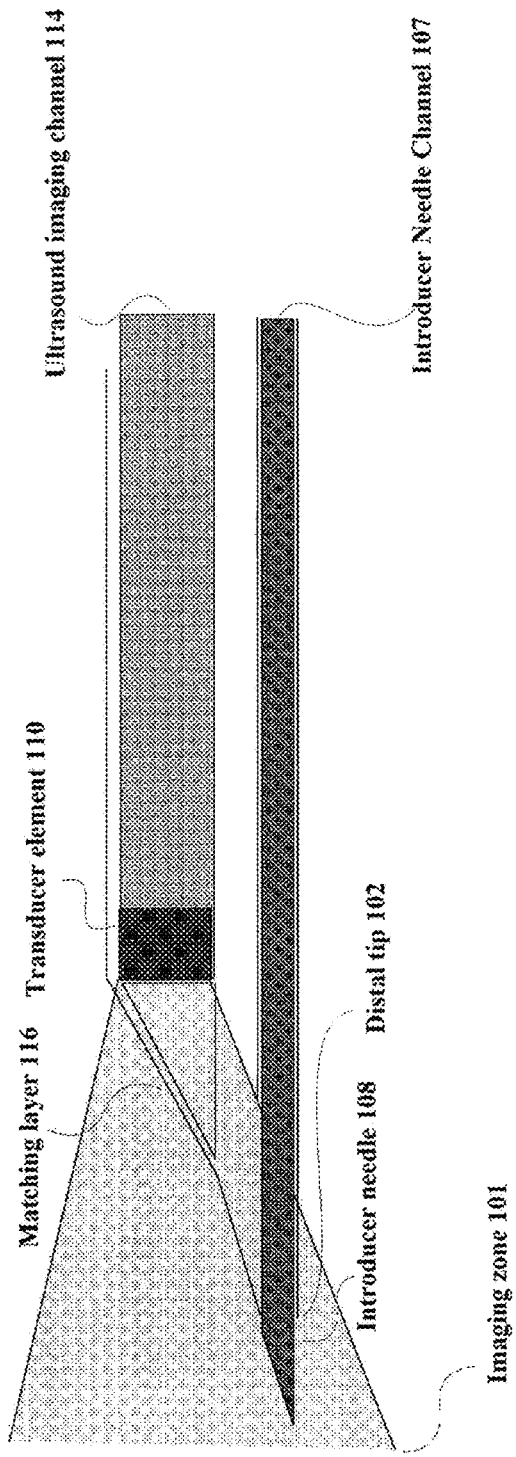
FIG. 1 depicts a view of a patient or distal end of an image guided catheter device assembly in accordance with one or more aspects described herein.

The aspects summarized above can be embodied in various forms. The following description shows, by way of illustration, combinations and configurations in which the aspects can be practiced. It is understood that the described aspects and/or embodiments are merely examples. It is also understood that other aspects and/or embodiments can be utilized, and that structural and functional modifications can be made, without departing from the scope of the present disclosure.

Minimally invasive procedures provide physicians with access to internal organs and structures via a small number of incisions in the patient's body. Minimally invasive procedures are generally preferable over open procedures because they require only small incisions, thus reducing trauma to the body, lessening recovery time, and reducing costs. The medical instruments used in performing such procedures are generally similar to those used in open surgical procedures except they include an extension such as a tubular extension of small outer diameter between the end of the instrument entering the surgical field (i.e., the operable end of the tool, instrument or device) and the proximal end portion having a large outer diameter gripped by the surgeon, the tubular extension being tapered and containing an imaging lumen and at least one other lumen, for example, for a syringe and introducer needle.

Typically, minimally invasive procedures involve up to five incisions up to one inch in length. The treatment area is then accessed by inserting one or more cannulas or sleeves through the incisions to provide entry ports through which instruments are passed. Alternatively, access to the treatment area can sometimes be obtained using a natural bodily opening such as the throat or rectum. In procedures using this approach, a cannula or sleeve is inserted into the bodily opening and surgical instruments are passed to the treatment site, either through the cannula/sleeve or directly through the bodily opening.

While minimally invasive procedures provide numerous advantages over open procedures, they generally do not provide a physician with a direct view of the targeted sites. Further, many parts of the anatomy are rather complex and/or small and thus require particular precision and delicate handling. It is therefore desirable to provide precise imaging techniques for use during minimally invasive procedures.

In general, the illustrated embodiments and aspects provide an image guided catheter device that couples an imaging system within an imaging lumen and an instrument delivery system and/or minimally invasive interventional device within a tapered lumen open from the proximal end to the tapered distal tip. The instrument delivery system can include, for example, delivery of materials to or from a target site or delivery of instruments and devices to a target site.

In accordance with aspects described herein, an ultrasound imaging device of this invention can comprise one or more small ultrasound transducers integrated into an imaging transducer assembly, either as forward-directed transducers for direct, head-on imaging or combined with one or more side-directed transducers (as taught in priority applications and issued patents) which can provide additional imaging or other ultrasound applications such as delivery of heat to a target site within the patient. In addition, such ultrasound imaging can also be combined with all-optical high resolution transducer imaging and provide optional optical imaging through the use of one or more fiber optic bundles disposed though the imaging transducer assembly in additional imaging lumens (not shown) but discussed in priority applications and patents. For example, a first low resolution, long range imaging transducer assembly may be replaced with a high resolution, short range imaging transducer assembly as the target site is reached in real time during a minimally invasive medical procedure.

An imaging system in accordance with aspects and features described herein can guide and facilitate many different procedures, thereby significantly assisting in the access of and performance of procedures on organs, structures and cavities within the body, particularly during minimally invasive procedures. The described devices and methods are compatible with all surgical and diagnostic devices and will allow bedside emergency procedures. Ultrasound provides particular benefits because it is biologically safe and uses non-radiating energy to provide detailed anatomic and, in some cases, functional images. The images generated by devices described herein can provide a user with direct vision within the body in real time. Further, ultrasound provides a user with visualization of structures as well as within and beyond structures (such as the pericardium).

In certain embodiments, the device can comprise an ultrasound imaging catheter that incorporates one or more variable frequency ultrasound transducer assemblies that replace an original transducer assembly operating at one or more frequency ranges within the frequency range of from 20 KHZ to, for example, several hundred MHz. In one preferred embodiment, one frequency range of one replaceable transducer assembly may be 5 mHz to 25 mHz. However, various frequency ranges of the replaceable ultrasound transducer assembly can be used for different purposes and provide different beneficial results. Frequencies in the lower range, for example, below 1 MHz, and particularly in the 100-200 KHz range, can be used, for example, to provide heat therapy or to treat conditions such as blood clots and provide low resolution, long range imaging. Frequencies above 1 MHz can be used to provide higher resolution, short range imaging. For example, frequencies in the 25-30 MHz range can be used to image organs such as the eye or can be used to provide imaging of small animals. Even higher frequency ranges, for example, ultrasound frequency ranges in the 100 to several hundred MHz range, can be used to provide very high-resolution imaging, sometimes known as high-frequency ultrasound microscopy for use in very close target sites such as at a heart valve with minimally invasive surgery replacing prior art open heart surgery.

Devices and methods such as are described herein are suitable for use in a variety of medical procedures. In certain embodiments, the image guided catheter device may comprise conventional catheter applications including, for example, biopsy catheters, ablation catheters, and mapping catheters, in combination with the novel imaging aspects of replaceable imaging frequencies and instruments imaged by the imaging components described herein. In other embodiments, the device can comprise one or more interventional devices (e.g. syringe, forceps, biopsy instruments, clamps, MEMS manipulators, retractors, etc.) that may be compatible with a catheter such as a biopsy catheter, ablation catheter, mapping catheter, or other form of sheath having larger lumens. In some embodiments, the device can also be compatible with instruments such as videoscopes, external wired or wireless ultrasound imaging and delivery needles such as those used for stem cell therapy. In still other embodiments, the devices can be compatible with fiber optics such as those used for vision therapy. U.S. patent application Ser. No. 11/871,219 filed Oct. 12, 2007 (now U.S. Pat. No. 8,147,413 issued Apr. 12, 2012, Ser. No. 12/182,247 filed Jul. 30, 2008 (now U.S. Pat. No. 8,038,622 issued Oct. 18, 2011), Ser. No. 12/283,779 filed Oct. 14, 2008 (now U.S. Pat. No. 8,147,414 issued Apr. 3, 2012), Ser. No. 12/700,066 filed Feb. 4, 2010 (now U.S. Pat. No. 8,235,903 issued Aug. 7, 2012), Ser. No. 13/847,902 filed Aug. 22, 2013 (now allowed) and Ser. No. 13/973,476 filed Aug. 22, 2013 all by Theodore P. Abraham are incorporated by reference as to their entire contents, and all medical devices and applications described therein may be adapted for use with the present invention and, for example, adapted to fit through the needle lumen or other additional lumen (not shown) of the present invention's expendable housing. Furthermore, all other features and functionalities described in all these patent applications may be incorporated into and may be combined with embodiments of the present invention.

The devices and methods of various embodiments of an imaging catheter such as those illustrated in FIGS. 1-10 and described herein can be used in various minimally invasive surgical procedures and in other diagnostic and therapeutic applications. One skilled in the art will appreciate that the aspects and embodiments of an imaging catheter as described herein, although advantageously suited for such procedures on humans, can have other uses, such as for veterinary procedures and open medical techniques as well as minimally invasive procedures in humans. Further, while the devices of the present invention are described with particular reference to catheters, this shall not be construed as limiting the devices to the these embodiments, as it is contemplated and thus within the scope of the illustrated devices to adapt the devices described herein so as to be in the form of any type of minimally invasive device (e.g. syringes, sheaths, wires, forceps, biopsy instruments, clamps, retractors, etc.).

Further, while certain devices, systems and methods are described herein with particular reference to pericardial access devices, systems, and methods, this shall not be construed as limiting, as it is contemplated to adapt the devices, systems and methods described herein so as to be used in any of a number of procedures, including, but not limited to: various cardiovascular procedures; general micro-surgery; biopsy, drug and device delivery; vascular procedures; urology; thoracic procedures; otorhinolaryngology (ear, nose and throat); orthopedic procedures; neurosurgery; gynecologic procedures; gastroenterologic and general procedures; colon and rectal procedures; pericardiocentesis; thoracentesis; ascites tap; ventricular lead placements; and electrical and electro-mechanical mapping of the heart. As such, it is contemplated that the specific design parameters, other characteristics set forth hereinafter, and methods in relation thereto can be modified to provide appropriate dimensions and geometries as required to perform such other techniques. For example, the length and diameter of the device as herein described is adapted to suit the particular conditions for a given procedure. Thus, the disclosure to follow should is illustrative only and should not be construed as limiting in any configuration of a device as described herein.

The device may be used to provide a three-dimensional mapping system solely using an incorporated ultrasound system or in connection with other imaging modalities such as computed tomography, magnetic resonance, videoscopy. When the device is in the form of a catheter or sheath, this will allow stereotactic and remote/robotic operation of devices inserted and manipulated through the device. In such a system, an imaging modality (ultrasound, CT or MRI) can be used to generate a three-dimensional image. The device can interactively use the generated images to be directed either manually or through an automated or semi-automated process for deployment to a target area displayed in the three-dimensional image. The device can be used in connection with an ultrasound display system (B mode image or 3D image) that interfaces with the device to produce and display the images.

Figure 7:
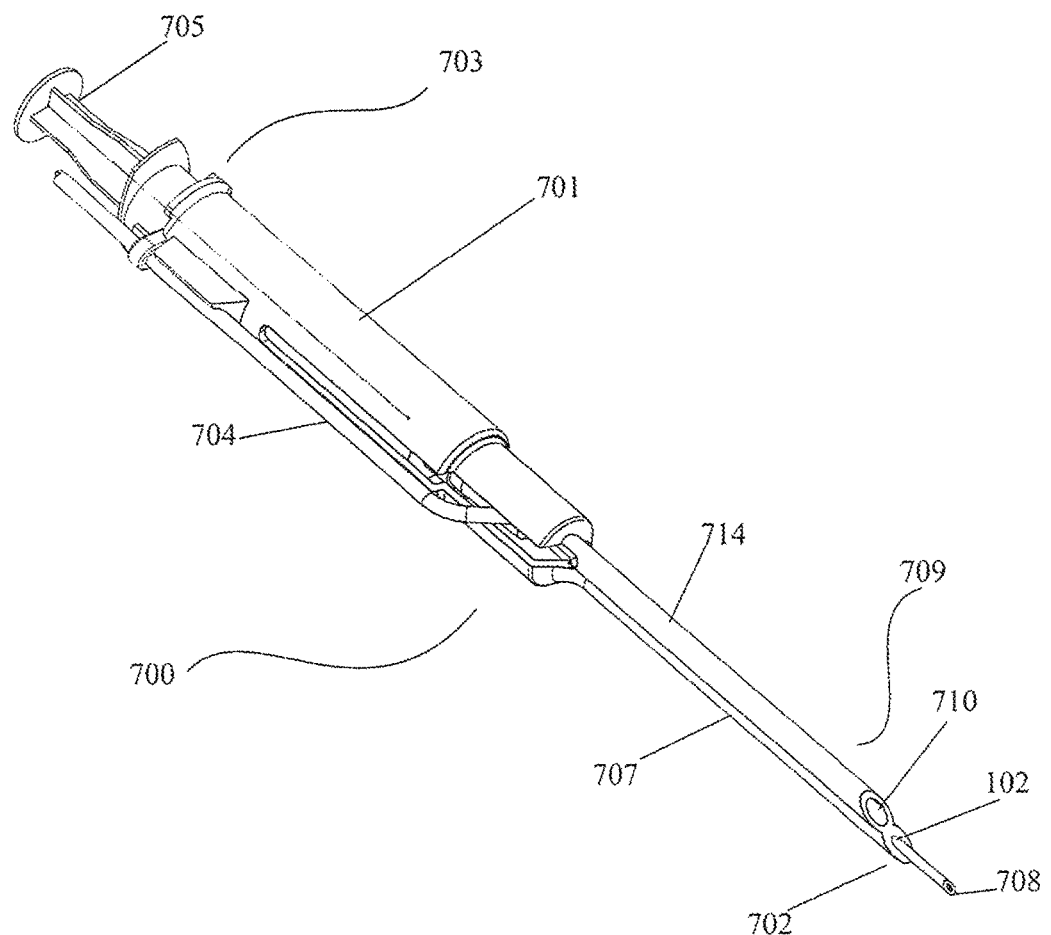
FIG. 7 depicts a fully assembled image guided catheter device showing an imaging ultrasound transducer assembly 704 and a syringe assembly 705 with a hollow (shown) or solid (not shown), preferably tapered, introducer needle 708 inserted into the expendable housing distal (patient) end 714.
Figure 10:
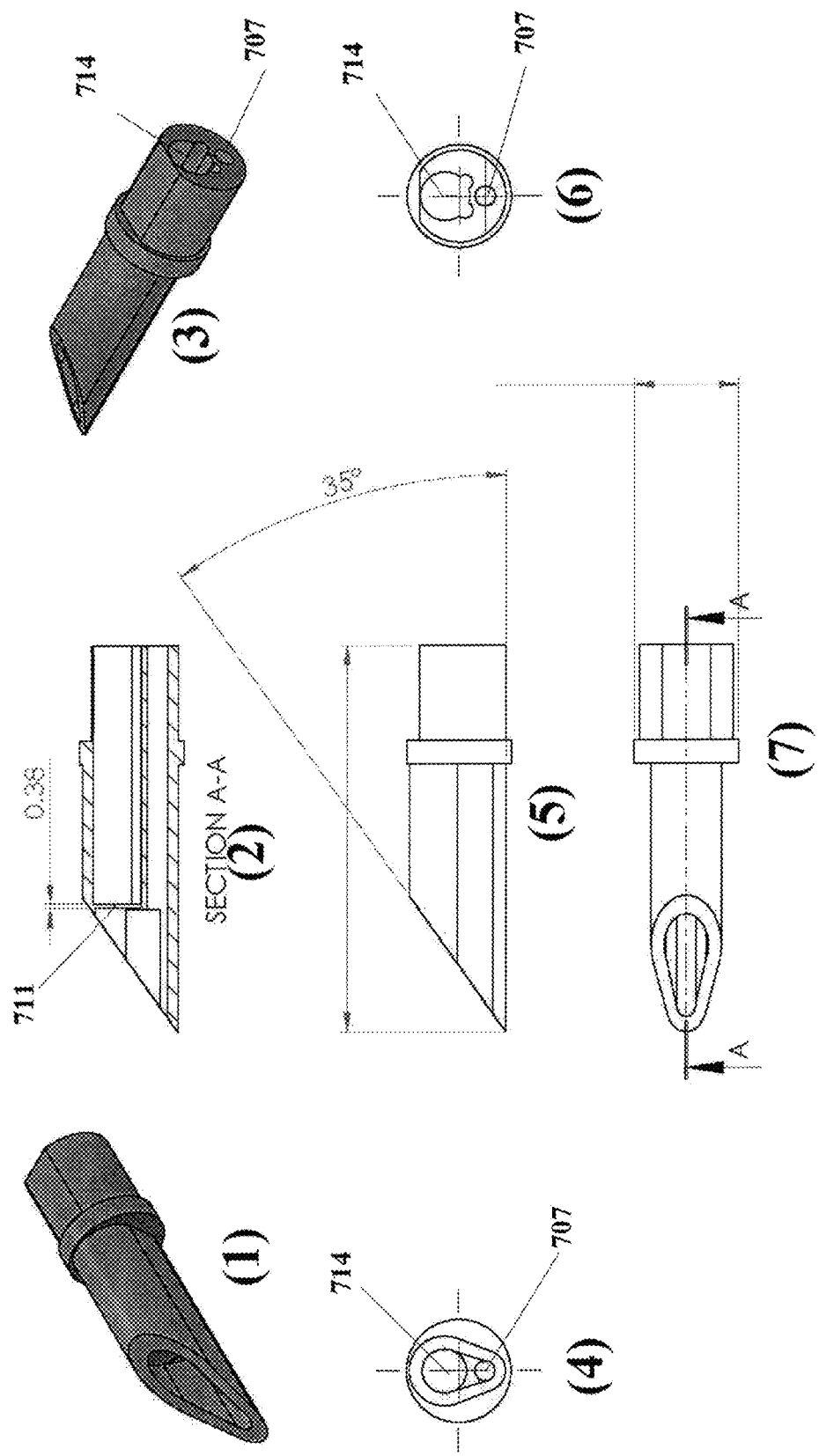
FIG. 10 depicts several views of an alternative embodiment of the distal tip of the expendable housing of an embodiment of the image guided catheter device.

By way of introduction, the fully assembled imaging device 700 of the present invention is depicted in FIG. 7. The present invention includes new embodiments of the imaging catheter of U.S. Ser. No. 13/847,902 with several new features and alternative embodiments in its design. In the present invention, the transducer element is placed closer to the introducer needle and the introducer needle placed in the center of the device to enable higher fidelity imaging. In one embodiment of the present invention as shown in FIG. 10, the image quality may be improved by placing a vertical window at the end of the imaging lumen instead of an angled window. Another important new feature is a reusable imaging transducer contained in a separate imaging transducer assembly. The image guided catheter device of the present invention comprises an expendable housing 701 with a proximal end 703 proximal to the healthcare professional using the device, a distal tip 702 that is inserted into a patient's body, an imaging lumen 714 and a needle lumen 707 of the distal end 709.

As shown in FIG. 7, an imaging ultrasound transducer assembly 704 is inserted into the left side of a housing 701 and pushed forward through the imaging lumen 714 toward the distal tip 702. The imaging transducer assembly 704 is inserted and secured into the housing 701 as described in FIG. 3A, FIG. 3B, FIG. 3C, FIG. 4A, and FIG. 4B. The transducer element 710 (not visible in FIG. 7) at the tip of the imaging transducer assembly may be positioned at a variable distance from the distal tip 702 such that the tip of the introducer needle 708 is within the imaging zone 101 of the transducer 710. The distal tip 702 has an end-on aperture 102 through which the introducer syringe/needle assembly 708 or other instrument is inserted for use with the image guided catheter device. The image guided catheter device is depicted in FIG. 7 with a syringe portion 705 inserted into the proximal end 703 such that an introducer needle 708 (hollow or solid) protrudes through the needle lumen 707 from the syringe.

In the image guided catheter device 700 of the present invention, the housing and syringe are disposable and the imaging transducer assembly may be separated from the device and reused. To reuse an imaging transducer assembly 704, the assembly may be covered with a disposable plastic cover while in use and sterilized between uses. The present invention is designed such that the imaging transducer assembly 704 has a curved shape that fits into a lengthwise slot on, for example, the left (or right) side of the housing, allowing the transducer assembly 704 to slide into the imaging lumen 714. The present invention may also include locking mechanisms to secure the imaging transducer assembly 704 and a syringe/needle assembly 705 or other interventional device to the proximal end 703 of the expendable housing 701.

The imaging transducer assembly 704 may also be freely removed and replaced at any time during a procedure. For example, a lower-frequency transducer assembly 704 adapted to produce images at a lower resolution but greater depth into the body may be used to find a target in a patient's internal organs. Once the target is found, the user can remove the lower-frequency range transducer assembly and replace it with a higher-frequency range transducer assembly 704 to produce a higher-resolution image at the target site allowing the user to obtain a better quality image while performing a procedure.

The expendable housing 701 may be a variable outer diameter rigid plastic catheter with diameter in the range of 1-20 French, with current preferred embodiments in the 10-14 French range (3.3667 to 4.6667 mm diameter). The imaging lumen 714 may have a larger outer diameter than that of the syringe/needle lumen 707. The imaging ultrasound transducer assembly 704 may comprise a forward viewing phased array probe with a variable field of view depending on the specific array. The imaging transducer assembly 704 may comprise an ultrasound transducer at the distal end (as seen in FIG. 2B) with variable frequency, variable cross-sectional diameter, and a variable number of transducer elements located in a steel or rigid plastic cylinder inside the expendable housing with a variable outer diameter. Examples of possible arrangements of transducer elements at the tip of the transducer are depicted in U.S. application Ser. No. 13/847,902, FIGS. 5A, 5B, and 5C. The present invention encompasses transducer assemblies 704 with frequency ranges in the kHz to mHz range, with a current preferred range of 5 mHz to 25 mHz for use in traveling from the skin to one to three centimeters beneath the skin. However, the frequency ranges may vary depending on the particular application for which the imaging device is used.

The dimensions of the device are not particularly limited and can vary depending on the ultimate use of the device, the insertion point, the obesity of the patient and the distance to the target area from the insertion point. The length of the device may vary depending on the application, but a preferred range is between one to four inches to be used, for example, for vascular applications, ranging up to twenty inches (ten inches for the proximal or surgeon end and ten inches for the distal end) to be used, for example, to perform procedures on the liver. The diameter and length of the tapered end near the distal tip 702 of the housing 701 can be affected by the size of an anatomical structure in which it is to be inserted. For example, the tapered distal end 709 can be longer and more slender for deep abdominal structures such as the kidneys or pelvic structures such as the ovaries or uterus, or can be shorter and wider for delivery of devices into more shallow structures such as a joint, muscle, the liver, or the heart. The diameter of the distal end can also be affected by the desired size of the incision through which device 700 is inserted and which must subsequently be closed. The diameter of the distal end can also be affected by the purpose for which the device is used. For example, the diameter of the distal end can be smaller for aspiration of fluids from a target site or larger if additional ports or device/medication delivery are desired.

For example, when device 700 is in the form of a vascular sheath (not shown), the outer diameter can vary depending on the targeted blood vessel through which the distal tip 702 is inserted. In an embodiment, device 700 can be in the form of vascular sheaths (not shown but exemplified in priority applications and patents) used during cardiac procedures and can be inserted through a blood vessel in the upper thigh or, alternatively, can be inserted through a blood vessel in the arm. In another embodiment, alternative devices 700 can be inserted by anesthetizing an area the patient's upper thigh and inserting the distal end 709 through a blood vessel in the upper thigh and towards the heart. In this embodiment, the distal end 709 can have a length sufficient to traverse this pathway, a diameter small enough and material flexible enough to be inserted into a blood vessel and advanced through the blood vessel to a target site. In an additional embodiment, the front end of the imaging transducer assembly 704 may be housed in a flexible material that would allow the front end of the ultrasound transducer to advance longer distances through a blood vessel along with a flexible distal end of the image guided catheter device 700. In a further embodiment, device 700 can have an introducer needle 708 integrated (not shown) therein (without using a syringe), which can enable device 700 to penetrate directly into the chest wall of a patient for direct access to the heart without the need for access through the vascular system.

Device 700 can also be in the form of a sheath (not shown) used during a laparoscopic procedure, and in such a case, the distal end 709 can generally have an outer diameter in accordance with conventional laparoscopic sheaths and will have a length that provides access to the target site.

Further, the device can be used as a minimally invasive conduit from the skin surface to the target site to allow passages of catheters, guide wires (not used in the depicted embodiment 700), and other instruments through distal tip 702, and the distal tip 702 can be sized to allow these various instruments to be passed therethrough. The user of the device may change the imaging transducer assembly 704 as needed during a procedure to obtain a better image, and the user may also change the instrument contained in the needle lumen 707 as needed to perform the procedure.

In an exemplary embodiment described in more detail herein, device 700 can be in the form of an image guided catheter 700 that can be introduced through the chest to access various internal structures using minimally invasive techniques. As such, the distal end 709 can have an outer diameter ranging from about 1 F to 15 F (wherein 1 F=0.33 mm) and a length ranging from about 1" to 20". Specific lengths and diameters can be provided based on the insertion site of the catheter, the distance to the desired target site(s), the obesity of the patient and the space required for insertion of one or more interventional devices through the distal tip 702.

In other embodiments, device 700 can be in the form of any interventional device that can be, for example, inserted through a sheath (not shown) or catheter to access various internal structures using minimally invasive techniques. As such, the distal tip 702 can have an outer diameter sized so as to fit within conventional sheaths or catheters, and a length suitable to access the desired target site(s) through the sheaths or catheters.

As shown in FIG. 1, the ultrasound transducer element 110 at the distal tip 102 of the device at the patient end has an imaging zone 101 encompassing the tip of the introducer needle 108. FIG. 1 shows an introducer needle lumen below an ultrasound imaging lumen 114. The removable imaging transducer assembly (not shown) may be inserted into the imaging lumen. To reduce ultrasound deflection during use of the device, as seen in FIG. 1, the imaging system can be provided with matching layers 116 disposed, for example, adjacent the front face of transducer element 110. Matching layers 116 can facilitate the matching of an impedance differential that may exist between the high impedance transducer elements and a low impedance patient. The structure of matching layers 116 can generally be in accordance with conventional matching layers and generally can include a matching layer front face and a matching layer rear face, and can optionally include a pocket with matching material that can reduce ultrasound deflection. Suitable matching layer materials can include, for example, plastic materials such as polysulfone or REXOLITE® (a thermoset material produced by crosslinking polystyrene with divinyl benzene, available from C-LEC Plastics, Inc., Beverly, N.J.). As shown in FIGS. 2B and 10, the diagonally oriented matching layer may be replaced with a vertical window at the front end of the imaging lumen to improve image quality. The diagonal matching layer may also be used in conjunction with a matching layer.

The imaging system may further include a backing layer (not shown) in accordance with conventional backing layers. The backing layers can generally be coupled to the rear face of the transducers 110 and function to attenuate acoustic energy that emerges from the rear face of the transducers 110. Generally, such backing layers can have a front face and a rear face, and can be fabricated of acoustic damping material that possesses high acoustic losses.

Transducers 110 can be of a size and composition in accordance with conventional transducers. For example, in some embodiments, the transducers 110 can comprise natural piezoelectric materials such as quartz, topaz, or tourmaline group minerals or can comprise man-made materials such as PZT ceramics or piezoelectric polymers such as Polyvinylidene fluoride (PVDF). In other embodiments and for high resolution and all-optic ultrasound transducer is useful. Transducers 110 can also be of any suitable size, with such size being limited by the desired size of the housing and the use which is being made of the ultrasound. i.e., for imaging or therapeutic purposes. In currently preferred embodiments, as many as 20-96 channels may be provided from the ultrasound transducer to the display output device through the ultrasound transducer assembly 704. However, further embodiments of the transducer assembly may contain anywhere from 1 to 2000 ultrasound imaging channels, with a greater number of parallel channels possible as ultrasound imaging technology progresses toward smaller elements such as, for example, fiber optics.

Figure 2A:
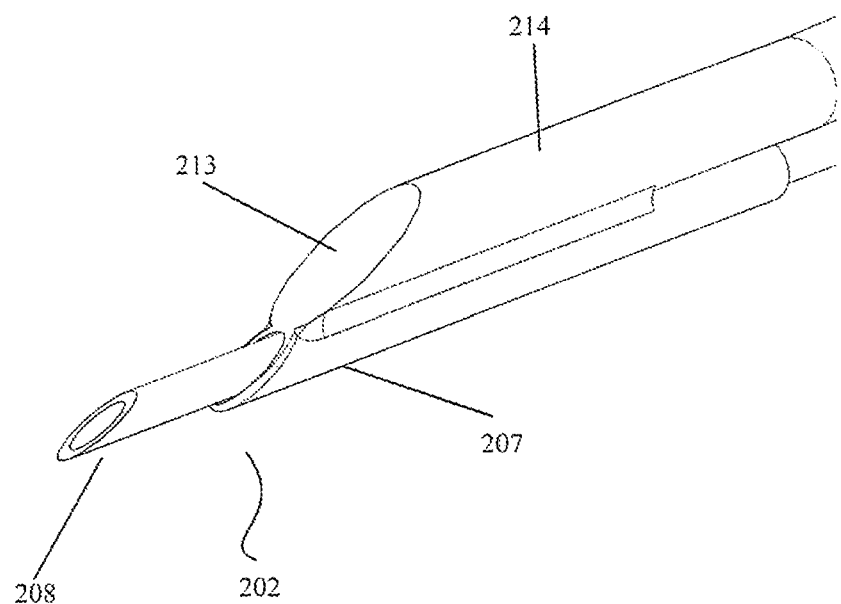
FIGS. 2A and 2B depict further side views of the patient or distal end of an imaging device in accordance with one or more aspects described herein.
Figure 2B:
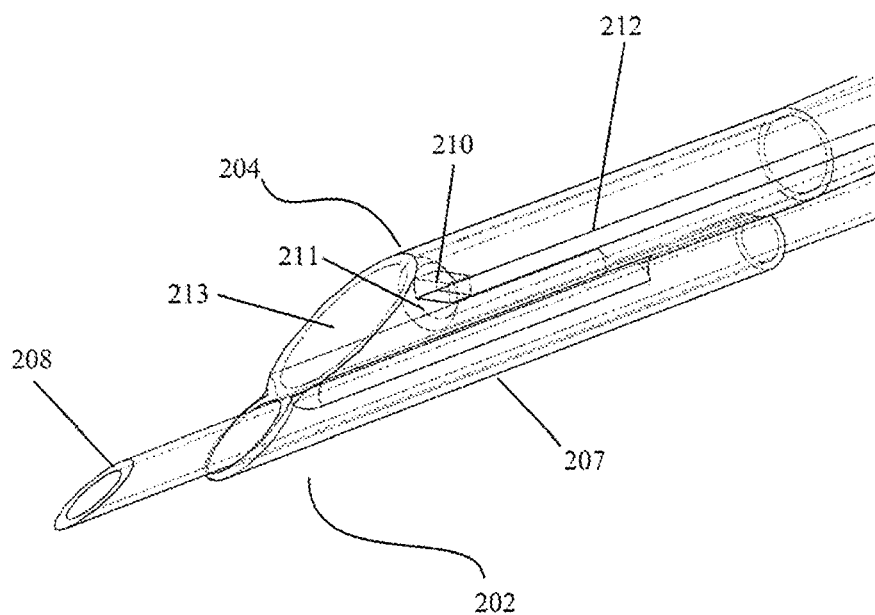

FIG. 2A shows a detailed view of the front end of the distal tip 202 of the device with an imaging lumen 214 on the top portion and an introducer needle 208 inside the needle lumen 207. FIG. 2B is the same front end of the distal tip 202 of the device, but FIG. 2B depicts the imaging lumen 214 and housing of the imaging transducer assembly 204 as transparent to demonstrate the internal structure of the transducer assembly. As shown in FIG. 2B, the imaging lumen may have a vertical window 211 in front of the front end of the imaging transducer assembly 204. Because ultrasound energy attenuates as it passes through an angled surface, placing a vertical window in front of the transducer assembly improves the quality of the image. The transducer assembly may comprise a transducer element 210 at the front end which can be of variable size and shape and contain a variable number of parallel imaging transducer channels. The transducer assembly also includes a conducting element 212 which, in a preferred embodiment, consists of a flexible cable that connects to a device for displaying the image. As shown in FIGS. 2A and 2B, the angled front end 213 of the imaging lumen 214 may be covered, either with a matching layer or another type of covering. In an alternative embodiment as depicted in FIG. 3A and FIG. 10, the angled front end 213 of the imaging lumen 214 may be open.

Conducting elements 212, which can control one or more transducers 210, can extend from the transducers 210 to the proximal end 202 of the elongate body 200 and can connect to an external system (ultrasound scanner) such as a gray scale color two-dimensional Doppler ultrasound system. Conducting elements 212 can cause the transducer to emit the sound waves and transmit sound waves reflected from tissues and structures to an ultrasound scanner where they can be transformed into a digital image. The conducting elements 212 can extend through the device 200 within the imaging lumen 214. The imaging lumen 214 can be provided in various sizes and, in exemplary embodiments, can range in size from 8-30 gauge. If a piezoelectric transducer system is used, the transducer assembly may, in a preferred embodiment, have 20 to 96 transducer channels at the front end that transmit data in parallel through the conducting element 212 to a display. In further embodiments, the transducer assembly may have anywhere from 1 to 2000 transducer channels. The number of transducer channels depends on the size of the transducer assembly, with a larger assembly having more channels and a smaller transducer assembly having fewer channels. In further embodiments, the transducer assembly may contain optical mapping technologies with considerably smaller transducer elements, which would allow a greater number of transducer channels in a smaller assembly. In another embodiment, the imaging transducer assembly or the expendable housing may further comprise a gyroscope or accelerometer (not shown) which enables the device to detect its spatial orientation inside the patient's body and adjust the ultrasound transducer image on the display screen according to the spatial orientation and position of the patient's body undergoing a medical procedure. For example, the image guided catheter of the present invention may be used to advantage by either left-handed or right-handed surgeons (the device 700 may be inserted upside-down, but the image remain right-side up).

Figure 3A:
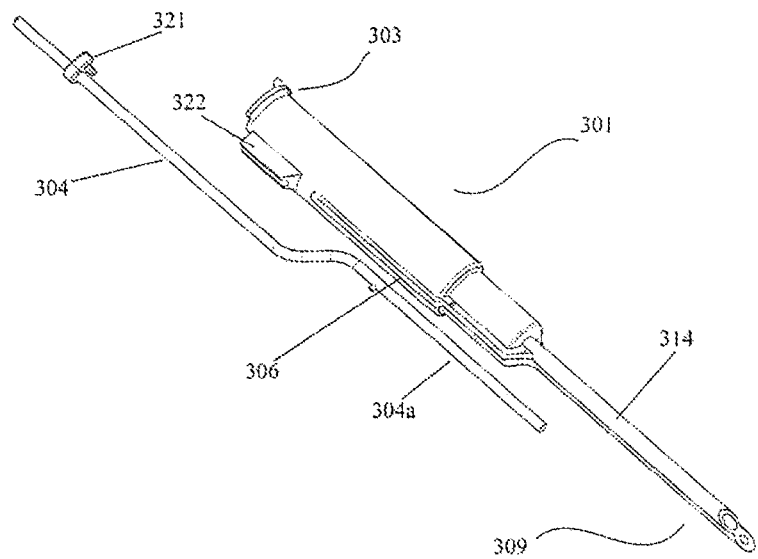
FIGS. 3A, 3B and 3C depict how a removable and replaceable imaging transducer assembly component may be inserted and moved into position into the imaging lumen at the distal end of the expendable housing.
Figure 3B:
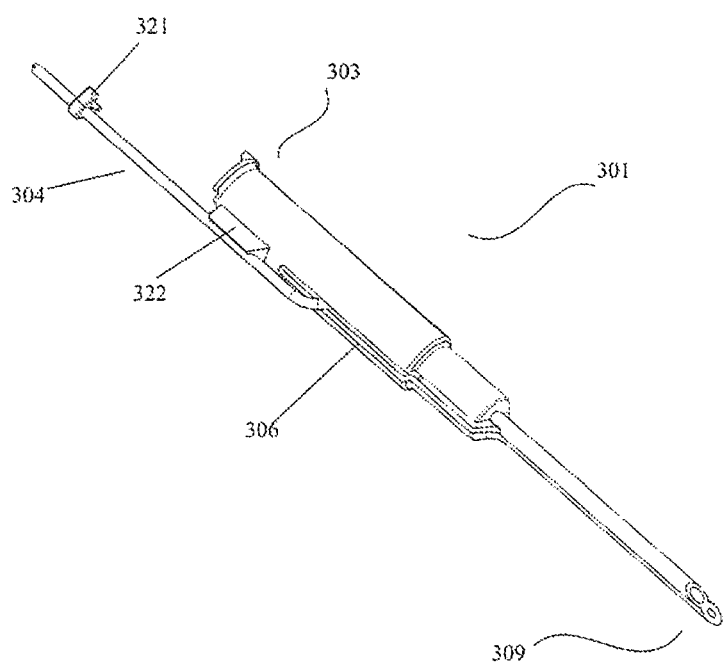
Figure 3C:
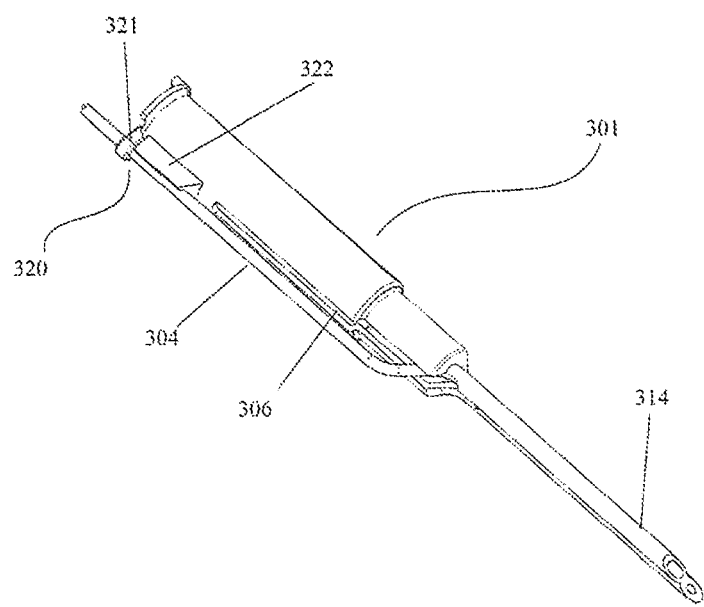

FIGS. 3A-3C demonstrate how an ergonomically designed S-shaped imaging transducer assembly 304 may be easily inserted and removed from the housing 301 through an opening 306 on the left side of the housing 301. FIG. 3A depicts the imaging transducer assembly 304 with its front portion 304a aligned with an opening 306 in the housing 301 of the device. The opening 306 connects to the imaging lumen 314 of the device. When the transducer assembly 304 is inserted horizontally into the opening 306 as depicted in FIG. 3B, the front end of the transducer assembly is aligned with the imaging lumen. Next, as seen in FIG. 3C, the transducer assembly is inserted into the imaging lumen 314 by pushing it vertically from the proximal end 303 to the distal end 309 of the device. FIG. 3C depicts the device fully assembled. Also depicted in FIG. 3A-3C is a transducer assembly locking mechanism 320 on the proximal end 303 of the device. The locking mechanism has a transducer portion 321 and a housing portion 322, which fit together to secure the transducer assembly when it is fully loaded into the housing.

Figure 4A:
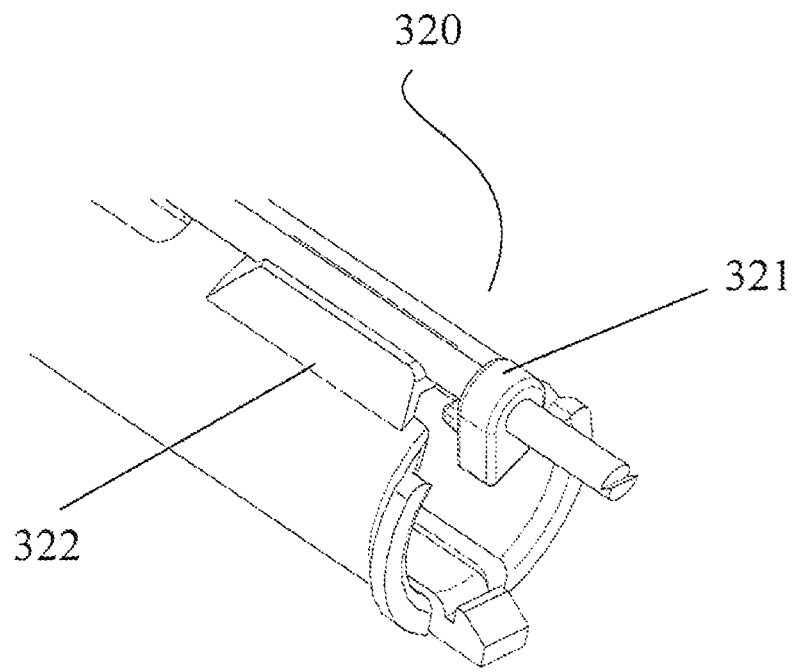
FIGS. 4A and 4B depict the locking mechanism for securing the imaging transducer assembly component to the expendable housing at the proximal end of the image guided catheter device.
Figure 4B:
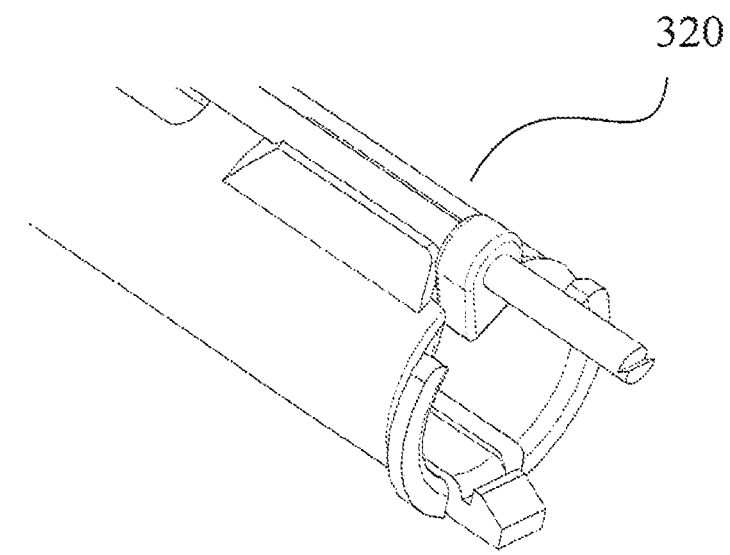

FIGS. 4A and 4B depict the transducer assembly locking mechanism. In FIG. 4A, the transducer portion 321 has a peg that fits into a slot in the housing portion 322 when the transducer assembly is inserted into the device. FIG. 4B shows the locking mechanism in a locked position.

Figure 5A:
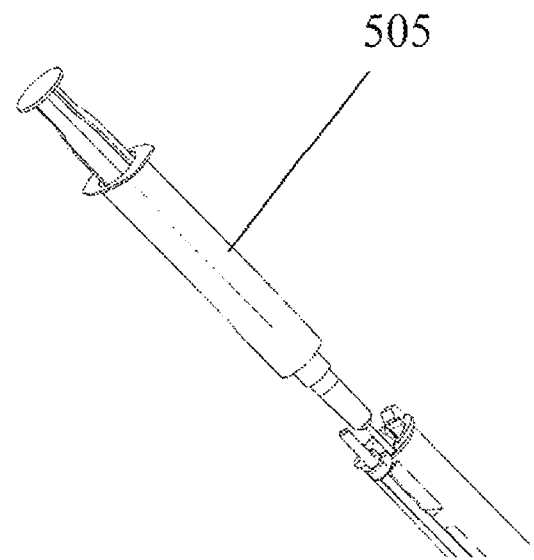
FIGS. 5A and 5B depict a further locking mechanism at the proximal or surgeon's end of the image guided catheter device assembly for, for example, securing a syringe having an introducer solid (not shown) or hollow needle or any other medical instrument that may be used in conjunction with the image guided catheter device to the expendable housing for, for example, performing a medical procedure.
Figure 5B:
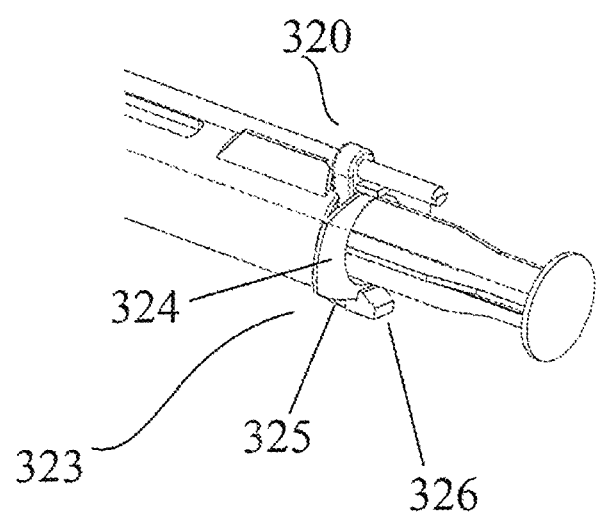
Figure 6A:
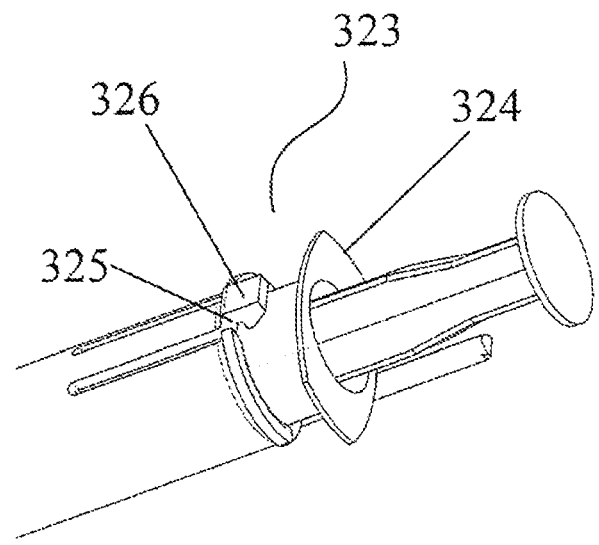
FIGS. 6A and 6B depict another view of the locking mechanism for securing a syringe or other medical device or instrument that may be used in conjunction with the image guided catheter device assembly at the proximal end of the expendable housing.
Figure 6B:
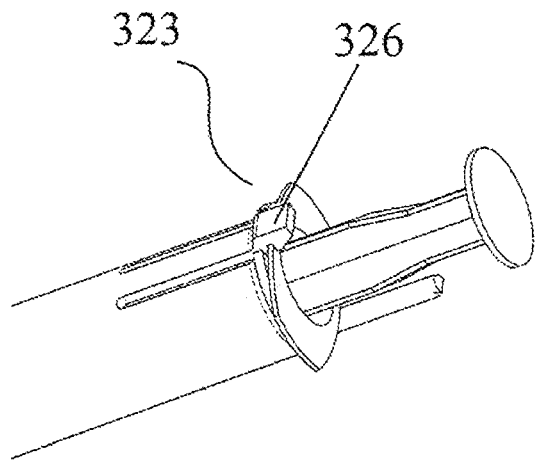

As depicted in FIGS. 5A, 5B, 6A, and 6B, the proximal end of the device may include a syringe locking mechanism 323 that secures a syringe or other interventional instrument to the device. The syringe locking mechanism 323 may be located across from the transducer locking mechanism 320 or at another location on the proximal end of the device. In one embodiment, an edge 324 of a syringe may lock into place by clicking into a groove 325 in a tab 326 that extends from the edge of the proximal end of the device. The syringe depicted in FIGS. 5A and 5B is intended to be an example, and interventional instruments other than a syringe may be adapted to be used with the device and secured in place by the syringe locking mechanism 323. As shown in FIG. 5B, the edge of the syringe further secures the transducer locking mechanism 320 by holding it in place when secured by the syringe locking mechanism 323. In alternative embodiments, the transducer locking mechanism may allow the user to remove or replace the imaging transducer assembly without first removing the syringe. For example, the transducer locking mechanism may project further out from the housing of the device.

Figure 8A:
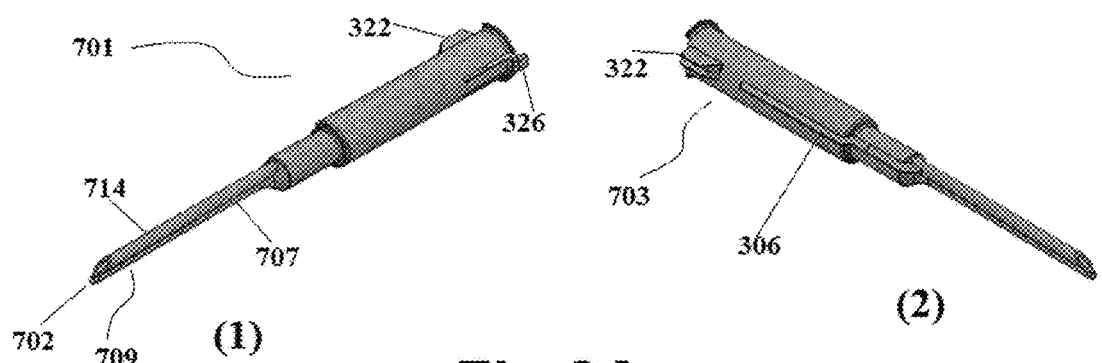
FIGS. 8A and 8B depict several views of the image guided catheter housing of the present invention.
Figure 8B:
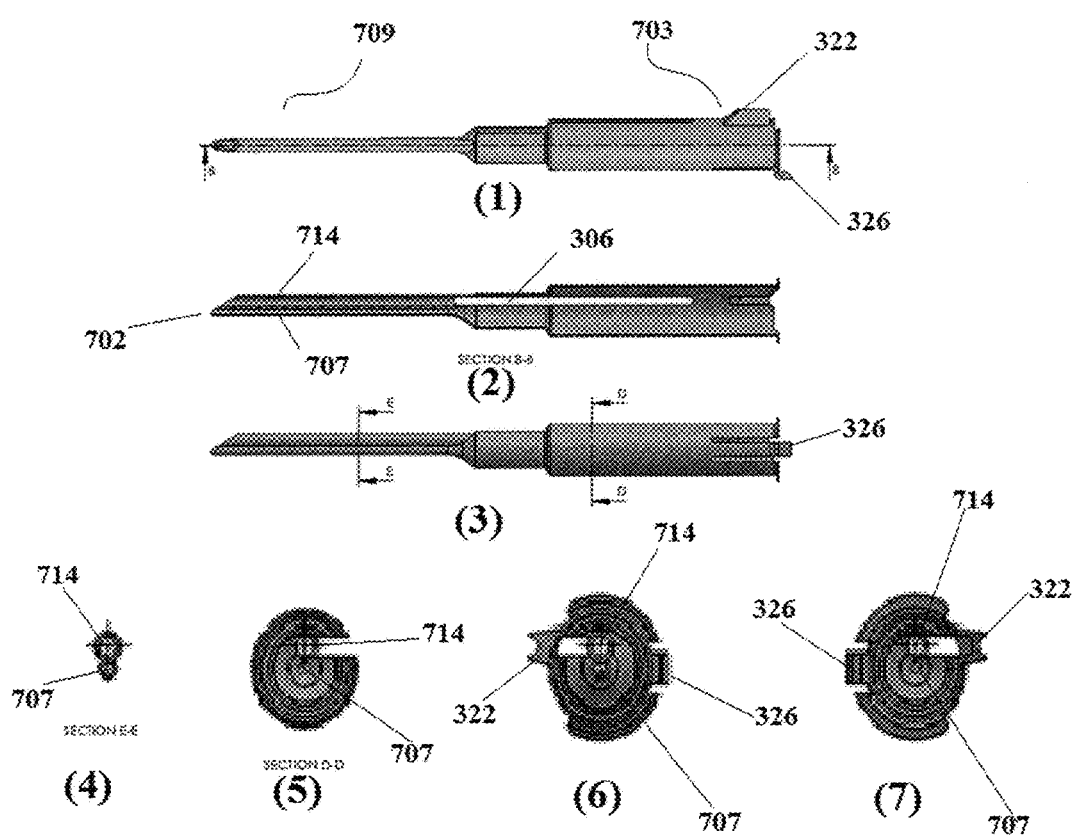

FIGS. 8A and 8B depict multiple views of the housing 701 of the device. FIG. 8A(1) is a right side view, while FIG. 8A(2) is a left side view. The housing 701 as depicted in FIG. 8A(1) and FIG. 8A(2) includes a transducer locking mechanism 322 and a syringe locking mechanism 326 at the proximal end 703, an opening 306 for an imaging transducer assembly on the left side of the housing 701, and an imaging lumen 714 and needle lumen 714 at the distal end 709. FIG. 8B(1) is a top view of the housing 701. FIG. 8B(2) is a vertical cross-section of the housing 701 demonstrating how the opening 306 aligns with the imaging lumen 714 and allows an imaging transducer assembly to be inserted into the device. FIG. 8B(3) is a right side view of the housing. FIG. 88B(4) is a horizontal cross-section of the housing at a location on the distal end 709 marked by the letters EE in FIG. 8B(3). FIG. 8B(5) is a horizontal cross-section of the housing at a location on the distal end 709 marked by the letters DD in FIG. 8B(3). FIG. 8B(6) is a horizontal front view of the housing depicting the distal end of the housing, and FIG. 88B(7) is a horizontal rear view depicting the proximal end of the housing. In FIGS. 8B(5) and 8B(6), the needle lumen 707 can be seen in the center, and the imaging lumen 714 is right above the needle lumen 707. In FIG. 8B(6), the transducer locking mechanism 322 is depicted on the left, and the syringe locking mechanism is depicted on the right.

Figure 9A:
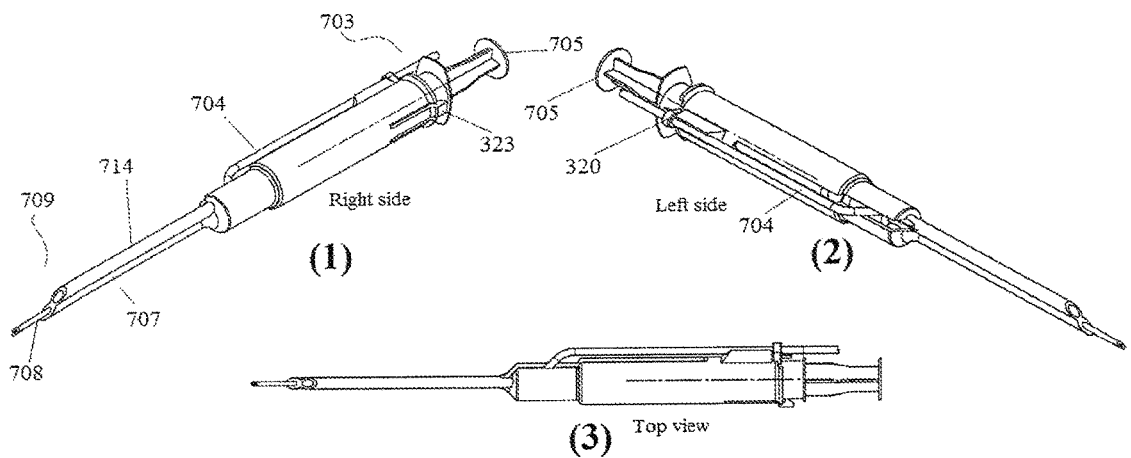
FIGS. 9A and 9B depict several views of a fully assembled imaging device including an expendable housing, a replaceable imaging transducer assembly, and a replaceable syringe with a tapered needle for introducing the device into a body or, if hollow, for removing fluids or tissue samples.
Figure 9B:
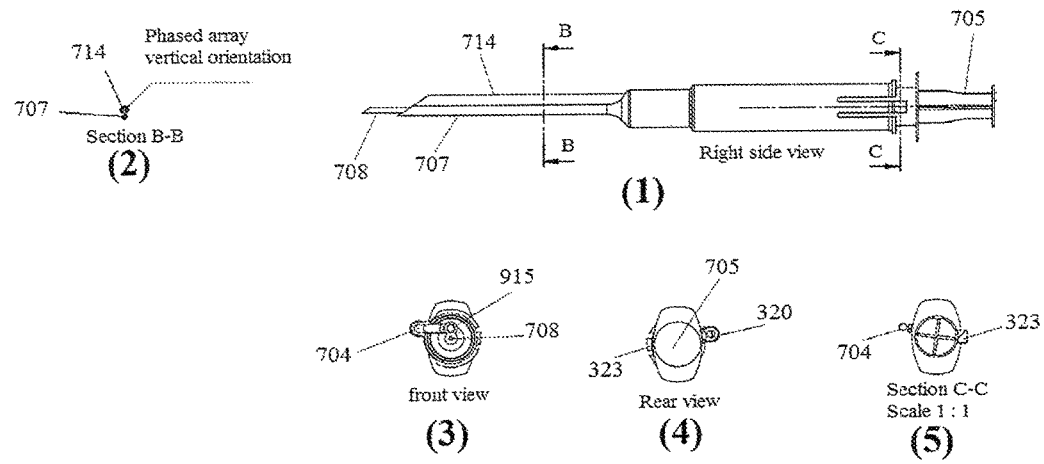

FIGS. 9A and 9B depict several views of a fully assembled device with a housing, an imaging transducer assembly 704, and a syringe 705. FIG. 9A(1) is a right side view, FIG. 9A(2) is a left side view, and FIG. 9A(3) is a top view. FIG. 9B depicts several horizontal cross-sections of the device. FIG. 9B(1) is a right side view marked with the letters B-B near the distal end 709 to show the location of the cross-section of FIG. 9B(2) and the letters CC near the proximal end 703 to show the location of the cross section shown in FIG. 9B(5). FIG. 9B(3) is a front view from the distal tip of the device showing the imaging transducer assembly 704 with a front end 915 directly above the introducer needle 708 and a syringe locking mechanism 323 on the right side. The introducer needle 908 is shown directly at the center of the device. FIG. 9B(4) is a rear view from the proximal end 703 of the device showing a syringe locking mechanism 323 and a transducer locking mechanism 320. As seen in all figures, the distal tip of the device which is introduced into a patient's body has a cone-shaped angled tip. As seen in FIG. 10(5), the angle of the distal tip is marked as 35 degrees from the horizontal, and this angle may be in a range of 20 to 80 degrees.

FIG. 10 shows multiple views of an embodiment of the distal tip of the device. FIGS. 10(1), and 10(5) show a right side view of the distal tip, FIG. 10(3) shows a left side view of the distal tip of the device, and FIG. 10(7) shows a top view of the distal tip of the device. FIG. 10(2) is a vertical cross-section of the distal tip as depicted in FIG. 10(7) marked by the letters A-A. FIG. 10(4) shows a front view of the distal tip and FIG. 10(6) shows a back view of the distal tip. As shown in FIG. 10(2), the width of the vertical window at the front end of the imaging transducer assembly is marked as 0.38 mm. In preferred embodiments, the vertical window's width may be in a range of 0.05 mm to 1.5 mm.

In some embodiments, device 700 can be steerable and externally controlled by the operator. In some embodiments, one or more Micro-Electro-Mechanical Systems (MEMS) devices can be incorporated into the device 700 to allow an operator to control aspects of the device. MEMS systems can include, for example, mechanical elements (beams, cantilevers, diaphragms, valves, plates, and switches), sensors, actuators, and electronics. Referring to FIG. 7A of U.S. patent application Ser. No. 13/847,902, a MEMS position manipulator 701 can be mounted on device 100 at a distal portion of device 100 to control a position of transducer 210 to, for example, standard position 702, Position A 702a or Position B 702b. In other embodiments, one or more MEMS devices can be provided to function as tiny sensors and actuators. For example, MEMS can be incorporated in the device for measuring and monitoring pressure in the stomach or other organs in which the catheter is inserted, and for measuring and monitoring blood pressure when performing cardiac catheterization.

In another embodiment, for example, as shown in FIG. 7B of U.S. patent application Ser. No. 13/847,902, a MEMS manipulator lead fixation device 703 can be provided to permit an operator to remotely access a portion of a device within a patient's body. For example, MEMS manipulator 703 can be used to screw in a lead for a pacemaker implanted in a patient. Alternatively, MEMS manipulator 703 can be used to operate a biopsy needle or to manipulate a suture-application device within a patient. It should be noted that these uses are exemplary only and that a device having a MEMS manipulator as described herein can be used to access or manipulate any device in a body or for any other suitable purpose.

In accordance with aspects described herein, a device 700 may have a biopsy instrument such as, for example, the biopsy device depicted in FIGS. 8A-8D of U.S. patent application Ser. No. 13/847,902. In such an embodiment, device 700 can be adapted for use in biopsy procedures including but not limited to myocardial biopsy, brain biopsy, muscle biopsy, lung biopsy, liver biopsy, kidney biopsy, uterine and ovarian biopsy, esophageal biopsy, stomach biopsy, intestinal biopsy, tumor biopsy (anywhere), targeted biopsy of potentially abnormal zones in any of the above items (e.g., ultrasound guided biopsy of an abnormal area in the liver or kidney with the present catheter will allow access to the abnormal area, identification of abnormal zones by deploying the ultrasound and biopsy instrument to the specific area of interest). As such, device 700 can, in some cases, be in the form of a catheter or sheath-like device that is insertable through small incisions in the body. A biopsy tool could be inserted through the needle lumen of the device.

In another embodiment, such as is shown in FIGS. 9A and 9B of U.S. patent application Ser. No. 13/847,902, device 700 can include a retrieval instrument in combination with a bioptome or other custom instrument. As is known in the art, a bioptome can comprise a specialized biopsy catheter for use in cardiac applications, particularly a catheter with a special end designed for obtaining endomyocardial biopsy samples. In use, a bioptome can be threaded through the needle lumen of the device 700 to the right ventricle, where it can snip small tissue samples from the septal wall for pathologic examination. In other uses, a bioptome tip device can be used to monitor heart transplantation patients for early signs of tissue rejection. In use, as seen in FIGS. 9A and 9B of U.S. patent application Ser. No. 13/847,902, a retrieval instrument having a bioptome 903 can be in closed position 901 at a distal end and closed position 904 at a proximal end to assist in inserting the instrument into the area of interest, and then can be placed into an open position 902 at the distal end so that the desired tissue can be retrieved for examination or testing. A tissue sample collected by either a retrieval instrument, a biopsy tool, or a bioptome may be removed for analysis either by threading the instrument out of the body through the needle lumen, or by removing the entire device from the patient's body along with the tissue sample.

Device 700 in accordance with one or more aspects described herein can have many different embodiments for many different uses within the scope and spirit of the present disclosure. Device 700 can be in the form of a catheter or sheath that provides entry into these various body spaces, thus allowing therapy delivery, intervention, placement of devices and diagnostics. Device 700 can also be in the form of interventional devices for use in procedures within these spaces. Such catheters, sheaths, and devices are well known, and, thus, the general features of device 700 for these embodiments can be in accordance with conventional devices.

In addition, when provided with one or more integrated transducers 210 and other components required to provide ultrasound imaging as described herein, device 700 can be used in a wide variety of procedures which can be made substantially safer and easier through the combination of imaging aspects with therapeutic aspects of the device.

In some embodiments, device 700 can be used to provide access vascular structures including arteries, veins, lymphatics, and to other hollow structures such as the gastrointestinal tract, genitourinary tract, and the respiratory system. As such, the device can be in the form of, for example, a vascular sheath (not shown, but shown in priority applications and patents). Such sheaths are well known, and, thus, the general features of device 700 for these embodiments can be in accordance with conventional devices.

In other embodiments, device 700 can be used in procedures in various body spaces such as the pleural peritoneal space, pericardial space, perisphinal space, pelvis, and cerebrospinal space. For example, the device can be adapted for use in paracentesis, biopsy of any intra abdominal or intrapelvic organ, prostate biopsy, biopsy of tumors or otherwise suspected abnormal structures within the pelvis and abdomen, diagnosis of endometriosis, treatment by chemicals, cells, bio-agents, physical energy (e.g., cryo, radiofrequency, heat, laser) of any pathology within the pelvis and abdomen, visualization and application of therapy within the genitourinary tract, and drainage of abnormal or normal collection of fluid in actual or potential space in the abdomen, pelvis or genitourinary tract. In other embodiments, device 700 can be in the form of a catheter which can be used to drain fluid from a patient's gall bladder or any other hollow or solid organ in the abdomen.

Other procedures that can be performed using device 700 include procedures relating to diagnosis and treatment of infertility, including following a woman's ovum to determine an appropriate time for harvest, harvesting the ovum, and assisting in or performing the delivery of the fertilized egg to the uterus.

In some embodiments, device 700 can be designed for use in cardiac or vascular procedures and for accessing various targets. For example, device 700 can be designed to provide access to various structures such as the coronary sinus and other cardiac venous structures. Exemplary procedures that can be performed using device 700 can include: epicardial biopsy; electronic mapping (endocardial or epicardial); electromechanical mapping (endocardial or epicardial); endocardial or epicardial ablation using any form of energy; cannulation or delivery of catheters, pacing leads, and interventional devices; and mapping and access to the fossa ovalis and patent foramen ovale to enable crossing the atrial septum and allowing transvenous access to the left side of the heart; pericardiocentesis; left ventricular lead placement; delivery of therapy (e.g., drugs, stem cells, laser therapy, or ultrasound energy); epicardial coronary artery bypass; valve repair and placement, delivery of cardiac shape modifying devices (e.g., ACORN®, or MYOSPLINT® devices); myocardial scar reconstruction; ventricular reconstruction; ventricular assist device placement; and the treatment by chemicals, cells, bio-agents, physical energy (e.g., cryo, radiofrequency, heat, laser) of any pathology within the pericardial space or myocardium or intracardiac. As such, device 700 can, in some cases, be in the form of a sheath-like device that is insertable through, for example, an incision in the patient's upper thigh and through a blood vessel all the way up to the heart. In such embodiments, guidewire can be provided within the device to guide the device to the target area. In other embodiments, the device can be inserted through the pericardial space through the use of an introducer needle integrated therein.

In other embodiments, device 700 can be in the form of a device that is used in performing a cardiac procedure such as a biopsy instrument or an instrument for valve repair. In this case, device 700 can be provided with one or more transducers, along with the other components required to provide ultrasound imaging using the transducers as discussed herein.

In other embodiments, device 700 can be in the form of devices for use in performing procedures on the musculoskeletal system and for accessing the musculoskeletal system. For example, device 700 can be used for treatment by chemicals, cells, bio-agents, or physical energy (cryo, radiofrequency, heat, laser) of any pathology within the joint cavity, joint components, or muscle and bone; visualization and application of therapy involving muscle, bone, and joint components, including a joint cavity; and drainage of abnormal or normal collection of fluid in actual or potential space in the muscle, bone, or joint components. In these embodiments, device 700 can be in the form of a catheter or sheath that provides access to the musculo-skeletal system, thus allowing therapy delivery, intervention, placement of devices and diagnostics. Device 700 can also be in the form of interventional devices for use in procedures on the musculo-skeletal system. Such catheters, sheaths, and devices are well known, and, thus, the general features of device 700 for these embodiments can be in accordance with conventional devices. Device 700 would further include one or more transducers, along with the other components required to provide ultrasound imaging using the transducers as discussed herein.

In some embodiments, device 700 can be in the form of devices for use in procedures on the brain and nervous system and for accessing the brain and nervous system. For example, such devices can be used for the treatment by chemicals, cells, bioagents, or physical energy (cryo, radiofrequency, heat, laser) of any pathology within the cranium and spinal and peri-spinal space including the vasculature contained within; visualization and application of therapy within the cranium, spinal, and peri-spinal space and all contained vasculature; drainage of abnormal or normal collection of fluid in actual or potential space in the cranium, spinal, and peri-spinal space and all contained vasculature; and for transcatheter delivery of interventional devices such as aneurysm clips, hematologic treatments, and any other drug or non drug therapy, either directly or via the vasculature or via any other hollow structure within the cranium, spinal, and peri-spinal space and all contained vasculature. In these embodiments, device 700 can be in the form of a catheter or sheath that provides access to the brain and system, thus allowing therapy delivery, intervention, placement of devices and diagnostics.

Device 700 can further be adapted for use in procedures on the nasal passages, sinuses, and pharynx and for accessing the nasal passages, sinuses, and pharynx. In these embodiments, device 700 can be in the form of a catheter or sheath that provides access to a desired site of the nasal passages, sinuses, and pharynx, thus allowing therapy delivery, intervention, placement of devices and diagnostics. Device 700 can also be in the form of interventional devices for use in procedures on the nasal passages, sinuses, and pharynx (e.g., devices for therapy delivery, intervention, placement of devices and diagnostics). Such catheters, sheaths, and devices are well known, and, thus, the general features of device 700 for these embodiments can be in accordance with conventional devices. Device 700 would further include one or more transducers, along with the other components required to provide ultrasound imaging using the transducers as discussed herein.

Device 700 can further be in the form of devices used to treat and address chronic problems and, as such, can be delivered and lodged in body cavities, organs, or other anatomic locations for long term monitoring or anatomy or function or dynamics including hemodynamics. In these examples, the device can be in the form of a catheter or sheath or other conventional chronic treatment or monitoring device that can be lodged at a desired site. Device 700 would further include one or more transducers 210, along with the other components required to provide ultrasound imaging using the transducers 210 as discussed herein. Device 700 can also be used for implanting a monitoring or drug delivery device at a specific site in the body using its imaging capabilities to assist the user in finding a precise target site.

In some embodiments, the present device 700 can further be integrated with other non-ultrasound imaging modalities including infrared, laser, optical coherence, fiber optic instruments including, but not limited to endoscopic mapping. For example, the imaging lumen can further be provided with a fiber optic lumen through which an optical fiber is insertable.

The devices 700 can be used to perform any variety of medical procedures including those set forth herein. The general features of these procedures is in accordance with conventional procedures and further make use of the integrated imaging system to provide visualization while accessing and performing procedures at the target site.

Access to other organs, structures, and spaces can be performed in similar fashion with appropriate procedural modifications specific for the particular organs, structures or spaces.

All documents mentioned herein are incorporated by reference herein as to any description which may be deemed essential to an understanding of illustrated and discussed aspects and embodiments of devices and methods herein.

Although the devices and methods discussed above and primarily illustrated and described herein provide instruments that also can be adapted for performing minimally invasive diagnostic or therapeutic procedures on humans, it will be appreciated by those skilled in the art that such instruments and methods also are adaptable for use in other surgical procedures as well as in performing various veterinary surgeries. Further, while several preferred embodiments have been described using specific terms, such description is for illustrative purposes only, and it is to be understood that changes and variations may be made without departing from the spirit or scope of the following claims.

What is claimed is:

1. An image guided catheter device configured to be used in minimally invasive medical procedures, the image guided catheter device comprising:

an elongate cylindrical housing configured to facilitate entry of the image guided catheter device through skin tissue of a human body, wherein the elongate cylindrical housing has an expendable housing component including a distal end and a reusable housing component including a proximal end, the proximal end having an outer diameter larger that an outer diameter of the distal end, wherein the expendable housing component has a tapered tip at the distal end, the tapered tip being configured to be directly inserted via the skin tissue and guidable to a target site within the human body during use of the image guided catheter device, wherein the expendable housing component has at least one closed longitudinal imaging lumen at the distal end and at least one longitudinal tool lumen, and wherein the at least one closed longitudinal imaging lumen at the distal end of the expendable housing component has an open longitudinal slot opening at the proximal end adjacent and connected to the at least one closed longitudinal imaging lumen at the distal end, the open longitudinal slot opening for receiving different removable, replaceable imaging transducer, fiber optic or optical coherence assemblies adapted to fit in the open longitudinal slot opening and slide forward to the distal end of the at least one closed longitudinal imaging lumen;

a first imaging element adapted to be disposed at a distal end of the at least one imaging transducer, optical fiber or optical coherence imaging assembly, the at least one closed longitudinal imaging lumen terminating at a peripheral location behind a tapered distal tip of a tapered tip of the distal end of the expendable housing component and adapted to receive the at least one removable, replaceable imaging transducer, fiber optic or optical coherence assembly at its proximal end longitudinal slot opening and slide forward into the at least one closed longitudinal imaging lumen to its distal end, and the imaging transducer, fiber optic or optical coherence assembly being electrically connected from the at least one closed longitudinal imaging lumen to an output display device;

said first imaging element being configured to provide forward-directed imaging in a direction of the distal end of the elongate cylindrical housing to include the distal tip of the tapered tip of the elongate cylindrical housing; and a removable, replaceable introducer tool disposed within the longitudinal tool lumen at an end-on aperture within the tapered distal tip of the tapered tip of the elongate cylindrical housing of the image guided catheter, the longitudinal tool lumen being parallel to the at least one closed longitudinal imaging lumen.

2. The image guided catheter device according to claim 1, wherein said elongate cylindrical housing comprises the at least one closed longitudinal imaging lumen at the distal end and said imaging transducer comprises an all-optical high resolution transducer arranged in said imaging lumen at the distal end and disposed proximate to a transverse window at the distal end of the at least one closed longitudinal imaging lumen of the elongate, cylindrical housing.

3. The image guided catheter device according to claim 2, wherein said elongate cylindrical housing has a tapered, open face at a distal end thereof and said imaging transducer assembly being disposed behind the transverse window of said tapered, open face when the imaging transducer assembly is disposed in said longitudinal slot opening and moved forward into the at least one closed longitudinal imaging lumen into a locked position with said elongate cylindrical housing.

4. The image guided catheter device according to claim 2, wherein said elongate cylindrical housing has a face at a distal end thereof and comprises one of an accelerometer and a gyroscope for providing an indication to a display device of a degree of spatial rotation and position of the image guided catheter device, the display device providing a spatial orientation of an image adapted to be compatible with a spatial orientation of a body subjected to treatment with the image guided catheter device during a medical procedure.

5. The image guided catheter device according to claim 1, wherein said elongate cylindrical housing has a flat tapered face at the distal end thereof.

6. The image guided catheter device according to claim 1, wherein a first ultrasound imaging transducer assembly is configured to operate at a frequency including one within a 20 KHz to 300 MHz frequency range and is adapted to be replaceable with a second ultrasound imaging transducer assembly operating at a frequency including one within a 5 MHz to 100 MHz frequency range.

7. The image guided catheter device according to claim 6, wherein said first ultrasound imaging transducer assembly operates at a frequency less than 1 MHz and is configured to provide therapeutic treatment to the human body during use of the image guided catheter device range and is adapted to be replaceable with a second ultrasound imaging transducer assembly operating at a frequency including one within a 5 MHz to 100 MHz frequency range and is further adapted to be replaceable with a third all-optical high resolution transducer imaging assembly during a medical procedure.

8. The image guided catheter device according to claim 6, wherein said first ultrasound imaging transducer assembly operates at a frequency above 1 MHz and is configured to provide forward-directed imaging within the body during use of the image guided catheter device and is adapted to be replaceable with a second ultrasound imaging transducer assembly operating at a frequency below 1 MHz during a medical procedure on the same patient.

9. The image guided catheter device according to claim 1, wherein said elongate cylindrical housing includes a sheath which contains a lumen, the sheath and lumen extending in a longitudinal direction along a length of said elongate cylindrical housing for receiving one of a syringe, an interventional instrument, a clamp, forceps, a retractor and a micro-electro-mechanical system, the sheath or lumen being hollow and parallel to the at least one closed longitudinal imaging lumen.

10. The image guided catheter device according to claim 9, the syringe having a hollow, tapered tip for one of extracting unwanted fluid and for delivering medication at the target site.

11. The image guided catheter device according to claim 9, further comprising a retrieval instrument disposed within a longitudinal lumen, the retrieval instrument replacing the syringe and the removable, replaceable introducer tool at the target site, wherein said first imaging element is configured to provide forward-directed imaging guidance for operation of said retrieval instrument during use of the image guided catheter device.

12. The image guided catheter device according to claim 11, said retrieval instrument comprising a bioptome.

13. The image guided catheter device according to claim 1, further comprising a syringe, the removable, replaceable introducer tool of the image guided catheter device adapted to he connected to said syringe, the syringe being configured to be clasped and removably fixed to the elongate cylindrical housing when in use, the removable, replaceable introducer tool being one of hollow or solid and being expendable after use during a medical procedure.

14. The image guided catheter device of claim 1 being configured for intracardiac treatment via pericardial access, the introducer tool being adapted to puncture a pericardium during use.

15. An image guided catheter device configured to be used in minimally invasive medical procedures, comprising:
an elongate housing having proximal and distal ends, the proximal end of the elongate housing having a larger outer diameter than the distal end, the elongate housing having a tapered tip at the distal end being configured to be directly inserted into a target site within a human body from body skin tissue proximate the target site during use of the image guided catheter device, said elongate housing having a lengthwise slot at the proximal end for receiving a removable, replaceable, imaging transducer assembly including an ultrasound transducer, and at least one closed, longitudinal lumen extending along a longitudinal axis of the distal end for receiving the ultrasound imaging transducer assembly, the at least one closed, longitudinal lumen connected to a longitudinal, open slot at its proximate end for receiving the ultrasound imaging transducer assembly and adapted for the imaging transducer assembly to slide forward into the at least one closed, longitudinal lumen until reaching its distal end;
a first imaging element disposed in the ultrasound imaging transducer assembly at a distal end, the ultrasound imaging transducer assembly for removable replacement and having a predetermined ultrasound frequency range, the ultrasound imaging transducer assembly distal end for introduction into the lengthwise open slot at the proximal end of the elongate housing and for slideable movement forward into the distal end of the elongate housing such that the first imaging element is proximate a window at the distal end of the elongate housing, said first imaging element including the ultrasound transducer for disposition at an outer periphery of the tapered tip of the elongate housing at the distal end of the at least one longitudinal lumen;
a removable, replaceable introducer tool disposed within an end-on aperture within the distal tip of the tapered tip of the elongate housing and within an introducer tool longitudinal lumen extending through the elongate housing from the proximal end to the distal tip, the introducer tool longitudinal lumen being parallel to the at least one closed, longitudinal lumen for receiving the removable, replaceable, imaging transducer assembly, the introducer tool longitudinal lumen extending through the elongate housing from the proximal end to the distal end for receiving a syringe including the removable, replaceable introducer tool.

16. The image guided catheter device according to claim 15, the introducer tool longitudinal lumen extending through the elongate housing from the proximal end to the distal tip, the introducer tool longitudinal lumen for receiving the removable, replaceable introducer tool, the introducer tool longitudinal lumen also adapted to be configured to permit introduction of a medical instrument for use at said target site to replace the removable, replaceable introducer tool once the image guided catheter device reaches the target site.

17. The image guided catheter of claim 15 wherein the removable, replaceable introducer tool comprises a micro-electro-mechanical system, the micro-electro-mechanical system being moveable upwards and downwards proximate the distal end.

18. An image guided catheter device configured to be used in minimally invasive medical procedures, comprising:
a disposable housing configured to facilitate entry of a catheter through skin tissue of a human body, the disposable housing having proximal and distal ends, said disposable housing having a tapered tip at the distal end, an elongate body of the image guided catheter device being configured to be directly inserted into a target site within the human body during use of the image guided catheter device and having at least one closed, longitudinal imaging lumen extending along a longitudinal axis of the distal end of the disposable housing, the proximal end of the disposable housing having a lengthwise slot for receiving a transducer assembly having an S-shape comprising a straight portion, a bend and a continued straight portion, the lengthwise slot of the disposable housing being connected to the at least one closed, longitudinal imaging lumen and adapted to receive the transducer assembly and permit the transducer assembly to slide forward into the at least one closed, longitudinal imaging lumen;
the transducer assembly being adapted to be replaceable and removable during a medical procedure on a patient and the transducer assembly comprising a proximal and a distal end, the distal end including an ultrasound transducer for insertion into the lengthwise slot of the disposable housing and for slideable movement forward into the at least one closed, longitudinal imaging lumen at the distal end of the disposable housing, and
a removable, replaceable introducer tool and syringe disposed within a forward-directed imaging zone of the ultrasound transducer of the transducer assembly via an end-on aperture of the tapered tip at the distal end, said removable, replaceable introducer tool and said image guided catheter device configured to be introduced into said human body simultaneously during use of the image guided catheter device during a medical procedure, said removeable, replaceable introducer tool being one of solid and hollow and being configured, under ultrasound forward-directed imaging guidance, to puncture a human body wall proximate to said target site and to directly access said target site during use of the image guided catheter device, the removable, replaceable introducer tool being disposed to extend from the end-on aperture of the tapered tip of the distal end of the disposable housing and being within said forward-directed imaging zone of said ultrasound transducer during use of the image guided catheter device.

19. The image guided catheter device of claim 18, further wherein said removeable, replaceable introducer tool is removable and replaceable at a surgical site with a medical instrument adapted to be introduced in replacement of the syringe and the removeable, replaceable introducer tool during a medical procedure on a patient.

20. The image guided catheter device of claim 18, wherein said disposable housing further includes at least one closed, longitudinal imaging lumen extending along the distal end of the disposable housing to a window on a tapered face of the distal end of the disposable housing for receiving replaceable imaging modalities comprising one of ultrasound transducers at different frequencies of operation, optical fibers and optical coherence assemblies.

21. The image guided catheter device of claim 18 further comprising one of an accelerometer and a gyroscope, the one of the accelerometer and the gyroscope adapted for sensing a present orientation and position of the image guided catheter device with reference to a spatial orientation and position of the patient undergoing a medical procedure and outputting orientation and position data of the image guided catheter device to a display for presenting an internal image adapted to be compatible with the spatial orientation and position of the body undergoing the medical procedure.

\* \* \* \* \*